(12) United States Patent
Millan

(10) Patent No.: US 11,172,693 B2
(45) Date of Patent: Nov. 16, 2021

(54) FEED ADDITIVE COMPOSITION

(71) Applicant: DUPONT NUTRITION BIOSCIENCES APS, Copenhagen (DK)

(72) Inventor: Luis Fernando Romero Millan, Rhenfelden (CH)

(73) Assignee: DuPont Nutrition Biosciences APS, Copenhagen (DK)

( * ) Notice: Subject to any disclaimer, the term of this patent is extended or adjusted under 35 U.S.C. 154(b) by 0 days.

(21) Appl. No.: 16/257,556

(22) Filed: Jan. 25, 2019

(65) Prior Publication Data

US 2019/0223470 A1    Jul. 25, 2019

Related U.S. Application Data

(62) Division of application No. 13/985,847, filed as application No. PCT/GB2012/050123 on Jan. 19, 2012, now abandoned.

(30) Foreign Application Priority Data

Feb. 18, 2011    (GB) .................................. 1102865.1

(51) Int. Cl.

| | | |
|---|---|---|
| A23K 40/10 | (2016.01) | |
| C12N 1/20 | (2006.01) | |
| C12N 9/16 | (2006.01) | |
| A23K 40/30 | (2016.01) | |
| A23K 10/18 | (2016.01) | |
| A23K 20/189 | (2016.01) | |
| A23K 50/75 | (2016.01) | |
| A23K 50/30 | (2016.01) | |
| A23K 50/60 | (2016.01) | |
| C12R 1/125 | (2006.01) | |

(52) U.S. Cl.
CPC .............. *A23K 40/10* (2016.05); *A23K 10/18* (2016.05); *A23K 20/189* (2016.05); *A23K 40/30* (2016.05); *A23K 50/30* (2016.05); *A23K 50/60* (2016.05); *A23K 50/75* (2016.05); *C12N 1/20* (2013.01); *C12N 1/205* (2021.05); *C12N 9/16* (2013.01); *C12Y 301/03026* (2013.01); *C12R 2001/125* (2021.05)

(58) Field of Classification Search
CPC . A23K 40/10; C12N 1/20; C12N 9/16; C12N 9/50
See application file for complete search history.

(56) References Cited

U.S. PATENT DOCUMENTS

| | | | |
|---|---|---|---|
| 5,612,055 A | 3/1997 | Bedford et al. | |
| 6,287,841 B1 | 9/2001 | Mulleners | |
| 6,436,451 B1 | 8/2002 | Slaugh | |
| 6,500,426 B1 * | 12/2002 | Barendse | C12N 9/16 |
| | | | 424/94.1 |
| 6,562,340 B1 * | 5/2003 | Bedford | C12N 15/80 |
| | | | 424/94.61 |
| 6,805,886 B2 | 10/2004 | Slaugh | |
| 7,754,459 B1 | 7/2010 | Kock | |
| 7,754,469 B2 | 7/2010 | Baltzley | |
| 2005/0255092 A1 | 11/2005 | Rehberger et al. | |
| 2007/0202088 A1 | 8/2007 | Baltzley | |
| 2008/0263688 A1 | 10/2008 | Lassen | |
| 2009/0280090 A1 | 11/2009 | Rehberger | |
| 2013/0330307 A1 | 12/2013 | Millan | |

FOREIGN PATENT DOCUMENTS

| | | |
|---|---|---|
| CN | 101181016 | 5/2008 |
| CN | 107518156 A | 12/2017 |
| EP | 2675285 A2 | 12/2013 |
| WO | WO1989/06270 | 7/1989 |
| WO | WO1989/06279 | 7/1989 |
| WO | WO1992/012645 | 8/1992 |
| WO | WO1992/19729 | 11/1992 |
| WO | WO1994/25583 | 11/1994 |
| WO | WO1997/016076 | 5/1997 |
| WO | WO1998/20115 | 5/1998 |
| WO | WO03/062409 | 7/2003 |
| WO | WO2004/085638 | 10/2004 |
| WO | WO2005/123034 | 12/2005 |
| WO | WO2006/037328 | 4/2006 |

(Continued)

OTHER PUBLICATIONS

U.S. Appl. No. 13/985,857; U.S. Appl. No. 15/773,363; U.S. Appl. No. 16/544,204 (Year: 2019).*
Skinner et al., "An Economic Analysis of the Impact of Subclinical (Mild) Necrotic Enteritis in Broiler Chickens", Avian Diseases, 54: 1237-1240, 2010 (Year: 2010).*
Chomczynski and Saachi, Single-step method of RNA isolation . . . extraction (1987; Anal. Biochem. 162:156-9).
Ravi Ndran V et al: II Response of broiler chickens to microbial phytase supplementation as influenced by dietary phytic acid and non-phytate phosphorous levels. II. Effects on apparent metabolisable energy, nutrient digestibility and nutrient retention, British Poultry Science, vol. 41, Jan. 1, 2000 (Jan. 1, 2000), pp. 193-200.
Hofacre et al., "Using Competitive Exclusion . . . to Control Necrotic Enteritis," 2003 J. Appl. Poult. Res. 12:60-64).
Ravindran V., Hew L. I., Ravindran G., Bryden W. L. 2005. "Apparent ileal digestibility of amino acids in dietary ingredients for broiler chickens", Anim. Sci. 81:85-97.

(Continued)

*Primary Examiner* — Ruth A Davis

(57) ABSTRACT

A feed additive composition comprising a direct fed microbial in combination with a protease, and a phytase, and a method for improving the performance of a subject or for improving digestibility of a raw material in a feed (e.g. nutrient digestibility, such as amino acid digestibility), or for improving nitrogen retention, or for improving the subject's resistance to necrotic enteritis or for improving feed conversion ratio (FCR) or for improving weight gain in a subject or for improving feed efficiency in a subject or for modulating (e.g. improving) the immune response of the subject or for promoting the growth of beneficial bacteria in the gastrointestinal tract of a subject, which method comprising administering to a subject a direct fed microbial in combination with a protease and a phytase.

7 Claims, 7 Drawing Sheets

(56) References Cited

FOREIGN PATENT DOCUMENTS

| WO | WO2006/038062 | 4/2006 |
|---|---|---|
| WO | WO2006/038128 | 4/2006 |
| WO | WO2006/043178 | 4/2006 |
| WO | WO2006037327 | 4/2006 |
| WO | WO2007/044968 | 4/2007 |
| WO | WO2007/112739 | 10/2007 |
| WO | WO2008/016214 | 2/2008 |
| WO | WO2008/092901 | 8/2008 |
| WO | WO2008/097619 | 8/2008 |
| WO | WO2009/129489 | 10/2009 |
| WO | WO2010122532 | 10/2010 |
| WO | WO2011/117396 | 9/2011 |

OTHER PUBLICATIONS

Garosi et al., "Defining best practice for microarray analyses in nutrigenomic studies," (2005; Br. J. Nutr. 93:425-32).

Wang J J et al: "Beneficial effects of Versazyme, a keratinase feed additive, on body weight, feed conversion, and breast yield of broiler chickens.", Journal of Appli ed Poultry Research, vol. 15, No. 4, 2006, p. 544.

Druyan et al., "Growth rate of ascites-resistant . . . lines," (2008; Poult. Sci. 87:2418-29).

Immerself et al.,, Rethinking our understanding of the pathogenesis of necrotic enteritis in chickens, Oct. 30, 2008, 32-36, vol. 17/ No. 1.

Lu Liu et al, "A Collection Of Information On Projects Relating To High-New Technology And FastTrack Patent Technology" , Patent Literature Press, 1996, vol. 1, pp. 743.

\* cited by examiner

FEED ADDITIVE COMPOSITION

CROSS-REFERENCE TO RELATED APPLICATIONS

This application is a divisional of U.S. patent application Ser. No. 13/985,847, filed Aug. 15, 2013, now abandoned, which is a National Stage entry under 35 U.S.C. § 271 of International Patent Application No. PCT/GB2012/050123, filed Jan. 19, 2012, which claims priority to United Kingdom Patent Application No. 1102865.1, filed Feb. 18, 2011, the disclosures of each of which are incorporated by reference in its entirety.

FIELD OF INVENTION

The present invention relates to methods for improving feed compositions using a direct fed microbial in combination with a specific combination of enzymes, and to a feed additive composition comprising a direct fed microbial in combination with a specific combination of enzymes. The present invention further relates to uses and kits.

BACKGROUND OF THE INVENTION

Supplemental enzymes are used as additives to animal feed, particularly poultry and swine feeds, as a means to improve nutrient utilization and production performance characteristics. Enzyme blends are available to improve the nutritional value of diets containing soybean meal, animal protein meals, or high fibre food by-products.

The concept of direct fed microbials (DFM) involves the feeding of beneficial microbes to animals, such as dairy cattle when they are under periods of stress (disease, ration changes, environmental or production challenges). Probiotics is another term for this category of feed additives. Probiotics or DFM have been shown to improve animal performance in controlled studies. DFM including direct fed bacteria and or yeast-based products.

Although combinations of DFMs with some enzymes have been contemplated, the interaction between DFMs and enzymes has never been fully understood. The present invention relates to novel specific combinations which surprisingly significantly improve production performance characteristics in animals.

SUMMARY OF INVENTION

A seminal finding of the present invention is that a DFM in combination with a protease and a phytase has significant beneficial effects on the performance of an animal.

In particular, a seminal finding of the present invention is that a DFM in combination with a protease and phytase has significant beneficial effects on the performance of an animal, including improving one or more of the following: feed conversion ratio (FCR), ability to digest a raw material (e.g. nutrient digestibility, such as amino acid digestibility), nitrogen retention, survival, carcass yield, growth rate, weight gain, feed efficiency animals resistance to necrotic enteritis, immune response of the subject, the growth of beneficial bacteria in the gastrointestinal tract of a subject.

Another surprising effect of the present invention is that it can reduce nutrient excretion in manure (e.g. reduce nitrogen and phosphorus) content of a subject's manure.

In one aspect, the present invention provides a feed additive composition comprising (or consisting essentially of or consisting of) a direct fed microbial in combination with a protease and a phytase.

In another aspect, the present invention provides a method for improving the performance of a subject or for improving digestibility of a raw material in a feed (e.g. nutrient digestibility, such as amino acid digestibility), or for improving nitrogen retention, or for avoiding the negative effects of necrotic enteritis or for improving feed conversion ratio (FCR) or for improving weight gain in a subject or for improving feed efficiency in a subject or for modulating (e.g. improving) the immune response of the subject or for promoting the growth of beneficial bacteria in the gastrointestinal tract of a subject or for reducing populations of pathogenic bacteria in the gastrointestinal tract of a subject, or for reducing nutrient excretion in manure, which method comprising administering to a subject a direct fed microbial in combination with a protease and a phytase.

A yet further aspect of the present invention is use of a direct fed microbial in combination with a protease and a phytase for improving the performance of a subject or for improving digestibility of a raw material in a feed (e.g. nutrient digestibility, such as amino acid digestibility) or for improving nitrogen retention) or for avoiding the negative effects of necrotic enteritis or for improving feed conversion ratio (FCR) or for improving weight gain in a subject or for improving feed efficiency in a subject or for modulating (e.g. improving) the immune response of the subject or for promoting the growth of beneficial bacteria in the gastrointestinal tract of a subject or for reducing populations of pathogenic bacteria in the gastrointestinal tract of a subject, or for reducing nutrient excretion in manure.

In a further aspect of the present invention there is provided a kit comprising a direct fed microbial, a protease, a phytase (and optionally at least one vitamin and/or optionally at least one mineral) and instructions for administration.

In another aspect the present invention provides a method of preparing a feed additive composition, comprising admixing a direct fed microbial with a protease and a phytase and (optionally) packaging.

In a yet further aspect the present invention provides feed or feedstuff comprising a feed additive composition comprising (or consisting essentially of or consisting of) a direct fed microbial in combination with a protease and a phytase.

A premix comprising a feed additive composition comprising (or consisting essentially of or consisting of) a direct fed microbial in combination with a protease and a phytase, and at least one mineral and/or at least one vitamin.

In another aspect, the present invention provides a method of preparing a feedstuff comprising admixing a feed component with a feed additive composition comprising (or consisting essentially of or consisting of) a direct fed microbial in combination with a protease and a phytase.

In a further aspect, the present invention relates to a feed additive composition for preventing and/or treating coccidiosis and/or necrotic enteritis in a subject.

The present invention yet further provides a method of preventing and/or treating necrotic enteritis and/or coccidiosis wherein an effective amount of a feed additive composition according to the present invention is administered to a subject.

DETAILED DESCRIPTION OF THE INVENTION

Figure 1:
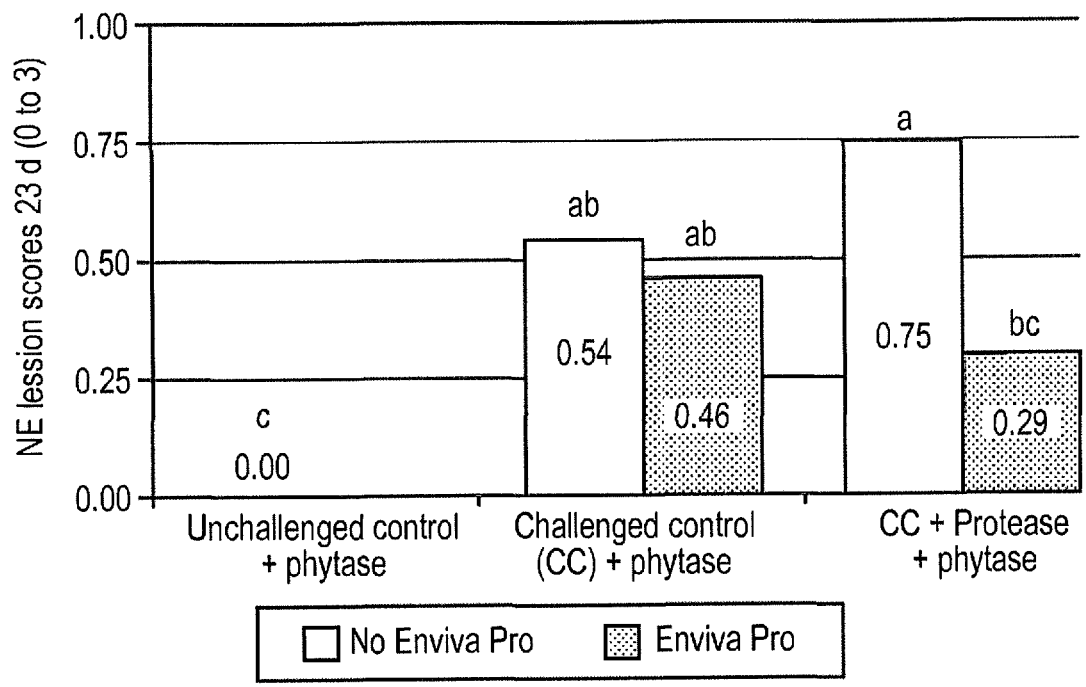
FIG. 1 shows that a combination of DFM (Enviva Pro® available from Danisco A/S) with a combination of a protease (e.g. *Bacillus subtilis* protease) and a phytase (e.g. 500 FTU/kg of Phyzyme XP (an *E. coli* phytase) available from Danisco A/S) significantly improved (reduced) necrotic enteritis lesion scores in the gut of the animals compared with the challenged control.

Preferably each of the enzymes used in the present invention are exogenous to the DFM. In other words the enzymes are preferably added to or admixed with the DFM.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" includes a plurality of such candidate agents and reference to "the feed" includes reference to one or more feeds and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

The enzymes for use in the present invention can be produced either by solid or submerged culture, including batch, fed-batch and continuous-flow processes. Culturing is accomplished in a growth medium comprising an aqueous mineral salts medium, organic growth factors, the carbon and energy source material, molecular oxygen, and, of course, a starting inoculum of one or more particular microorganism species to be employed.

Direct Fed Microbial (DFM)

The term "microbial" herein is used interchangeably with "microorganism".

Preferably the DFM comprises a viable microorganism. Preferably the DFM comprises a viable bacterium or a viable yeast or a viable fungi.

Preferably the DFM comprises a viable bacteria.

The term "viable microorganism" means a microorganism which is metabolically active or able to differentiate.

In one embodiment the DFM may be a spore forming bacterium and hence the term DFM may be comprised of or contain spores, e.g. bacterial spores. Therefore in one embodiment the term "viable microorganism" as used herein may include microbial spores, such as endospores or conidia.

In another embodiment the DFM in the feed additive composition according to the present invention is not comprised of or does not contain microbial spores, e.g. endospores or conidia.

The microorganism may be a naturally occurring microorganism or it may be a transformed microorganism. The microorganism may also be a combination of suitable microorganisms.

In some aspects, the DFM according to the present invention may be one or more of the following: a bacterium, a yeast, a fungi.

Preferably the DFM according to the present invention is a probiotic microorganism.

In the present invention, the term direct fed microbial (DFM) encompasses direct fed bacteria, direct fed yeast, direct fed fungi and combinations thereof.

Preferably the DFM is a direct fed bacterium.

Preferably the DFM is a combination comprising two or more bacteria, e.g. three or more or four or more; or the DFM is a combination comprising two or more bacterial strains, e.g. three or more or four or more.

Preferably the bacterium or bacteria is or are isolated.

Suitably the DFM may comprise a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* and combinations thereof.

In one embodiment the DFM may be selected from the following *Bacillus* spp: *Bacillus subtilis, Bacillus cereus, Bacillus licheniformis* and *Bacillus amyloliquefaciens*.

In one embodiment the DFM may be a combination comprising two or more *Bacillus* strains.

In one embodiment the DFM may be a combination of two or more the *Bacillus subtilis* strains 3A-P4 (PTA-6506); 15A-P4 (PTA-6507); 22C-P1 (PTA-6508); 2084 (NRRL B-500130); LSSA01 (NRRL-B-50104); BS27 (NRRL B-50105); BS 18 (NRRL B-50633); and BS 278 (NRRL B-50634).

Strains 3A-P4 (PTA-6506), 15A-P4 (PTA-6507) and 22C-P1 (PTA-6508) are publically available from American Type Culture Collection (ATCC).

Strains 2084 (NRRL B-500130); LSSA01 (NRRL-B-50104); BS27 (NRRL B-50105) are publically available from the Agricultural Research Service Culture Collection (NRRL). Strain *Bacillus subtilis* LSSA01 is sometimes referred to as *B. subtilis* 8.

These strains are taught in US 7, 754, 469 B2.

*Bacillus subtilis* BS 18 and *Bacillus subtilis* BS 278 were deposited by Andy Madisen of W227 N752 Westmound Dr. Waukesha, Wis. 53186, USA for Danisco USA Inc. of W227 N752 Westmound Dr. Waukesha, Wis. 53186, USA under the Budapest Treaty at the Agricultural Research Service Culture Collection (NRRL) at 1815 North University Street, Peoria, Ill. 61604, United States of America, under deposit numbers NRRL B-50633 and NRRL B-50634, respectively on 9 Jan. 2012.

Andy Madisen of W227 N752 Westmound Dr. Waukesha, Wis. 53186, USA and Danisco USA Inc. of W227 N752 Westmound Dr. Waukesha, Wis. 53186, USA authorise Danisco A/S of Langebrogade 1, PO Box 17, DK-1001, Copenhagen K, Denmark to refer to these deposited biological materials in this patent application and have given unreserved and irrevocable consent to the deposited material being made available to the public.

In some embodiments the DFM may be a combination comprising the *Bacillus subtilis* strains as detailed in the table below:

| B. subtilis strain | Bs 2084 | Bs 8 (LSSAO1) | Bs 3A-P4 | Bs 15A-P4 | Bs 278 | Bs 18 | Bs 22C-P1 |
|---|---|---|---|---|---|---|---|
| DFM Combination comprises | X | X | X | X | | | |
| | X | X | X | | | | |
| | X | X | | | X | | |
| | X | X | | X | | | |
| | X | | X | X | | | |
| | | X | X | X | | | |
| | X | X | | | | X | |
| | | | X | X | | | X |
| | X | X | | | | X | |

In one embodiment the DFM may be selected from the following *Lactococcus* spp: *Lactococcus cremoris* and *Lactococcus lactis* and combinations thereof.

In one embodiment the DFM may be selected from the following *Lactobacillus* spp: *Lactobacillus buchneri, Lactobacillus acidophilus, Lactobacillus casei, Lactobacillus kefiri, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sakei, Lactobacillus reuteri, Lactobacillus fermentum, Lactobacillus farciminis, Lactobacillus lactis, Lactobacillus delbreuckii, Lactobacillus plantarum, Lactobacillus paraplantarum, Lactobacillus farciminis, Lactobacillus rhamnosus, Lactobacillus crispatus, Lactobacillus gasseri, Lactobacillus johnsonii* and *Lactobacillus jensenii*, and combinations of any thereof.

In one embodiment the DFM may be selected from the following *Bifidobacteria* spp: *Bifidobacterium lactis, Bifidobacterium bifidium, Bifidobacterium longum, Bifidobacterium animalis, Bifidobacterium breve, Bifidobacterium infantis, Bifidobacterium catenulatum, Bifidobacterium pseudocatenulatum, Bifidobacterium adolescentis,* and *Bifidobacterium angulatum*, and combinations of any thereof.

Suitably the DFM may comprise a bacterium from one or more of the following species: *Bacillus subtilis, Bacillus licheniformis, Bacillus amyloliquefaciens, Enterococcus faecium, Enterococcus* spp, and *Pediococcus* spp, *Lactobacillus* spp, *Bifidobacterium* spp, *Lactobacillus acidophilus, Pediococsus acidilactici, Lactococcus lactis, Bifidobacterium bifidum, Bacillus subtilis, Propionibacterium thoenii, Lactobacillus farciminis, Lactobacillus rhamnosus, Megasphaera elsdenii, Clostridium butyricum, Bifidobacterium animalis* ssp. *animalis, Lactobacillus reuteri, Bacillus cereus, Lactobacillus salivarius* ssp. *Salivarius, Propionibacteria* sp and combinations thereof.

The direct fed bacterium used in the present invention may be of the same type (genus, species and strain) or may comprise a mixture of genera, species and/or strains.

Suitably the DFM according to the present invention may be one or more of the products or the microorganisms contained in those products as in the Table below:

| Product Name | Company | Microorganism(s) | Symbiotic ingredients |
| --- | --- | --- | --- |
| Enviva Pro ®. (formerly known as Avicorr ®) | Danisco A/S | *Bacillus subtilis* strain 2084 Accession No. NRR1 B-50013, *Bacillus subtilis* strain LSSAO1 Accession No. NRRL B-50104 and *Bacillus subtilis* strain 15A-P4 ATCC Accession No. PTA-6507 | |
| Calsporin ® | Calpis - Japan | *Bacillus subtilis* Strain C3102 | |
| Clostat ® | Kemin Industries Inc. | *Bacillus subtilis* Strain PB6 | |
| Cylactin ® | DSM | *Enterococcus faecium* NCIMB 10415 (SF68) | |
| Gallipro ® & GalliproMax ® | Chr. Hansen A/S | *Bacillus subtilis* Strain C3102 | |
| Gallipro ®Tect ® | Chr. Hansen A/S | *Bacillus licheniformis* | |
| Poultry star ® | Biomin, Inc | *Enterococcus* and *Pediococcus* | Fructo-oligosaccharides |
| Protexin ® | Protexin Int | *Lactobacillus, Bifidobacterium* and another | |
| Proflora ® | Alpharma Inc. | *Bacillus subtilis* strain QST 713 | β-Mos β-mannan oligosaccharides and β-glucans |
| Ecobiol ® & Ecobiol ® Plus | Norel S.A. | *Bacillus amyloliquefaciens* CECT-5940 | |
| Fortiflora ® | | *Enterococcus faecium* SF68 | |
| BioPlus2B ® | DSM | *Bacillus subtilis* and *Bacillus licheniformis* | |
| Lactiferm ® | Chr. Hansen | Lactic acid bacteria 7 *Enterococcus faecium* | |
| CSI ® | Danisco A/S | *Bacillus* strain | |
| Yea-Sacc ® | Alltech | *Saccharomyces cerevisiae* | |
| Biomin IMB52 ® | Biomin | *Enterococcus faecium* | |
| Biomin C5 ® | Biomin | *Pediococcus acidilactici, Enterococcus faecium, Bifidobacterium animalis* ssp. *animalis, Lactobacillus reuteri Lactobacillus salivarius* ssp. *salivarius* | |
| Biacton ® | ChemVet | *Lactobacillus farciminis* | |
| Oralin E1707 ® | Chevita GmBH | *Enterococcus faecium* | |
| Probios-pioneer PDFM ® | Chr Hansen | *Enterococcus faecium* (2 strains) *Lactococcus lactis* DSM 11037 | |
| Sorbiflore ® | Danisco Animal Nutrition | *Lactobacillus rhamnosus* and *Lactobacillus farciminis* | |
| Animavit ® | KRKA | *Bacillus subtilis* | |
| Bonvital ® | Lactosan GmbH | *Enterococcus faecium* | |
| Levucell SB 20 ® | Lallemand | *Saccharomyces cerevisiae* | |
| Levucell SC 0 & SC10 ® ME | Lallemand | *Saccharomyces cerevisiae* | |
| Bactocell | Lallemand | *Pediococcus acidilacti* | |
| ActiSaf ® (formerly BioSaf ®) | Le Saffre | *Saccharomyces cerevisiae* | |
| Actisaf ® SC47 | Le Saffre | *Saccharomyces cerevisiae* NCYC Sc47 | |
| Miya-Gold ® | Miyarisan Pharma | *Clostridium butyricum* | |
| Fecinor and Fecinor Plus ® | Norel S.A | *Enterococcus faecium* | |
| InteSwine ® | ntegro Gida ve Ticaret AS represented by RM Associates Ltd | *Saccharomyces cerevisiae* NCYC R-625 | |
| BioSprint ® | ProSol SpA | *Saccharomyces cerevisia* | |
| Provita ® | Provita | *Enterococcus faecium* and *Lactobacillus rhamnosus* | |
| PepSoyGen-C ® | Regal BV (Nutraferma) | *Bacillus subtilis* and *Aspergillus oryzae* | |

-continued

| Product Name | Company | Microorganism(s) | Symbiotic ingredients |
|---|---|---|---|
| Toyocerin ® | Rubinum | *Bacillus cereus* | |
| TOYOCERIN ® | Rubinum | *Bacillus cereus* var. *toyoi* NCIMB 40112/CNCM I-1012 | |

In one embodiment suitably the DFM may be Enviva Pro®. Enviva Pro® is commercially available from Danisco A/S and is a combination of *Bacillus* strain 2084 Accession No. NRR1 B-50013, *Bacillus strain* LSSAO1 Accession No. NRRL B-50104 and *Bacillus* strain 15A-P4 ATCC Accession No. PTA-6507 (as taught in U.S. Pat. No. 7,754,469 B—incorporated herein by reference).

Suitably, the DFM may comprise a yeast from the genera: *Saccharomyces* spp.

Preferably the DFM to be used in accordance with the present invention is a microorganism which is generally recognised as safe and, which is preferably GRAS approved.

A skilled person will readily be aware of specific species and or strains of microorganisms from within the genera described herein which are used in the food and/or agricultural industries and which are generally considered suitable for animal consumption.

Preferably, the DFM used in accordance with the present invention is one which is suitable for animal consumption.

Advantageously, where the product is a feed or feed additive composition, the viable DFM should remain effective through the normal "sell-by" or "expiration" date of the product during which the feed or feed additive composition is offered for sale by the retailer. The desired lengths of time and normal shelf life will vary from feedstuff to feedstuff and those of ordinary skill in the art will recognise that shelf-life times will vary upon the type of feedstuff, the size of the feedstuff, storage temperatures, processing conditions, packaging material and packaging equipment.

In some embodiments it is important that the DFM is tolerant to heat, i.e. is thermotolerant. This is particularly the case where the feed is pelleted. Therefore in one embodiment the DFM may be a thermotolerant microorganism, such as a thermotolerant bacteria, including for example *Bacillus* spp.

In some embodiments it may be preferable that the DFM is a spore producing bacteria, such as *Bacilli*, e.g. *Bacillus* spp. *Bacilli* are able to from stable endospores when conditions for growth are unfavorable and are very resistant to heat, pH, moisture and disinfectants.

In one embodiment suitably the DFM may decrease or prevent intestinal establishment of pathogenic microorganism (such as *Clostridium perfringens* and/or *E. coli* and/or *Salmonella* spp and/or *Campylobacter* spp.).

The DFM according to the present invention may be any suitable DFM. In one embodiment the following assay "DFM ASSAY" may used to determine the suitability of a microorganism to be a DFM. For the avoidance of doubt in one embodiment a DFM selected as an inhibitory strain (or an antipathogen DFM) in accordance with the "DFM ASSAY" taught herein is a suitable DFM for use in accordance with the present invention, i.e. in the feed additive composition according to the present invention.

DFM Assay:
Tubes were seeded each with a representative pathogen from a representative cluster.

Supernatant from a potential DFM grown aerobically or anaerobically was added to the seeded tubes and incubated.

After incubation, the optical density (OD) of the control and supernatant treated tubes was measured for each pathogen.

Colonies of (potential DFM) strains that produced a lowered OD compared with the control were classified as an inhibitory strain (or an antipathogen DFM).

The DFM assay as used herein is explained in more detail in US2009/0280090—incorporated herein by reference.

Preferably the representative pathogen used in assay is one (or more) of the following: *Clostridium*, such as *Clostridium perfringens* and/or *Clostridium difficile*, and/or *E. coli* and/or *Salmonella* spp and/or *Campylobacter* spp. In one preferred embodiment the assay is conducted with one or more of *Clostridium perfringens* and/or *Clostridium difficile* and/or *E. coli*, preferably *Clostridium perfringens* and/or *Clostridium difficile*, more preferably *Clostridium perfringens*.

In one embodiment the DFM of the present invention is preferably an antipathogen.

The term "antipathogen" as used herein means that the DFM counters an effect (e.g. a negative effect) of a pathogen.

In one embodiment to determine if a DFM is an antipathogen in accordance with the present invention the above mentioned DFM assay may be used. A DFM is considered to be an antipathogen or an antipathogen DFM if it is classed as an inhibitory strain in the above mentioned DFM assay, particularly when the pathogen is *Clostridium perfringens*.

In one embodiment the antipathogen DFM may be one or more of the following bacteria:
*Bacillus subtilis* strain 2084 Accession No. NRRL B-50013,
*Bacillus subtilis* strain LSSAO1 Accession No. NRRL B-50104,
*Bacillus subtilis* strain 15A-P4 ATCC Accession No. PTA-6507,
*Bacillus subtilis* strain 3A-P4 ATCC Accession No. PTA-6506, and
*Bacillus subtilis* strain BS27 ATCC Accession No. NRRL B-50105. For the avoidance of doubt these strains are available and are referred to in U.S. Pat. No. 7,754,459 B.

In one embodiment the DFM used in accordance with the present invention is not *Lactobacillus gasseri* BNR 17 Strain Acc No. KCTC 10902BP as taught in WO2008/016214.

Preferably the DFM is not an inactivated microorganism.

In one embodiment the DFM as used here is a composition comprising one or more DFM microorganisms as described herein. The composition may additionally comprise the enzymes of the present invention. The composition can be fed to an animal as a direct-fed microbial (DFM). One or more carrier(s) or other ingredients can be added to the DFM. The DFM may be presented in various physical forms, for example, as a top dress, as a water soluble concentrate for use as a liquid drench or to be added to a milk replacer, gelatin capsule, or gels. In one embodiment of the top dress form, freeze-dried fermentation product is added to a carrier, such as whey, maltodextrin, sucrose, dextrose, limestone (calcium carbonate), rice hulls, yeast culture, dried starch, and/or sodium silico aluminate. In one embodiment of the water soluble concentrate for a liquid drench or milk replacer supplement, freeze-dried fermentation product is added to a water soluble carrier, such as whey, maltodextrin, sucrose, dextrose, dried starch, sodium silico aluminate, and a liquid is added to form the drench or the supplement is added to milk or a milk replacer. In one embodiment of the gelatin capsule form, freeze-dried fermentation product is added to a carrier, such as whey, maltodextrin, sugar, limestone (calcium carbonate), rice hulls, yeast culture dried starch, and/or sodium silico aluminate. In one embodiment, the bacteria and carrier are enclosed in a degradable gelatin capsule. In one embodiment of the gels form, freeze-dried fermentation product is added to a carrier, such as vegetable oil, sucrose, silicon dioxide, polysorbate 80, propylene glycol, butylated hydroxyanisole, citric acid, ethoxyquin, and/or artificial coloring to form the gel.

The DFM(s) may optionally be admixed with a dry formulation of additives including but not limited to growth substrates, enzymes, sugars, carbohydrates, extracts and growth promoting micro-ingredients. The sugars could include the following: lactose; maltose; dextrose; maltodextrin; glucose; fructose; mannose; tagatose; sorbose; raffinose; and galactose. The sugars range from 50-95%, either individually or in combination. The extracts could include yeast or dried yeast fermentation solubles ranging from 5-50%. The growth substrates could include: trypticase, ranging from 5-25%; sodium lactate, ranging from 5-30%; and, Tween 80, ranging from 1-5%. The carbohydrates could include mannitol, sorbitol, adonitol and arabitol. The carbohydrates range from 5-50% individually or in combination. The micro-ingredients could include the following: calcium carbonate, ranging from 0.5-5.0%; calcium chloride, ranging from 0.5-5.0%; dipotassium phosphate, ranging from 0.5-5.0%; calcium phosphate, ranging from 0.5-5.0%; manganese proteinate, ranging from 0.25-1.00%; and, manganese, ranging from 0.25-1.0%.

To prepare DFMs described herein, the culture(s) and carrier(s) (where used) can be added to a ribbon or paddle mixer and mixed for about 15 minutes, although the timing can be increased or decreased. The components are blended such that a uniform mixture of the cultures and carriers result. The final product is preferably a dry, flowable powder. The DFM(s) or composition comprising same can then be added to animal feed or a feed premix, added to an animal's water, or administered in other ways known in the art (preferably simultaneously with the enzymes of the present invention). A feed for an animal can be supplemented with one or more DFM(s) described herein or with a composition described herein.

By "a mixture of at least two strains," is meant a mixture of two, three, four, five, six or even more strains. In some embodiments of a mixture of strains, the proportions can vary from 1% to 99%. Other embodiments of a mixture of strains are from 25% to 75%. Additional embodiments of a mixture of strains are approximately 50% for each strain. When a mixture comprises more than two strains, the strains can be present in substantially equal proportions or in different proportions in the mixture.

The DFM may be dosed appropriately.

Suitably dosages of DFM in the feed may be between about $1 \times 10^3$ CFU/g feed to about $1 \times 10^9$ CFU/g feed, suitably between about $1 \times 10^4$ CFU/g feed to about $1 \times 10^8$ CFU/g feed, suitably between about $7.5 \times 10^4$ CFU/g feed to about $1 \times 10^7$ CFU/g feed.

In one embodiment the DFM is dosed in the feedstuff at more than about $1 \times 10^3$ CFU/g feed, suitably more than about $1 \times 10^4$ CFU/g feed, suitably more than about $7.5 \times 10^4$ CFU/g feed.

Suitably dosages of DFM in the feed additive composition may be between about $1 \times 10^5$ CFU/g composition to about $1 \times 10^{13}$ CFU/g composition, suitably between about $1 \times 10^6$ CFU/g composition to about $1 \times 10^{12}$ CFU/g composition, suitably between about $3.75 \times 10^7$ CFU/g composition to about $1 \times 10^{11}$ CFU/g composition.

In one embodiment the DFM is dosed in the feed additive composition at more than about $1 \times 10^5$ CFU/g composition, suitably more than about $1 \times 10^6$ CFU/g composition, suitably more than about $3.75 \times 10^7$ CFU/g composition.

In one embodiment the DFM is dosed in the feed additive composition at more than about $2 \times 10^5$ CFU/g composition, suitably more than about $2 \times 10^6$ CFU/g composition, suitably more than about $3.75 \times 10^7$ CFU/g composition.

As used herein the term "CFU" means colony forming units and is a measure of viable cells in which a colony represents an aggregate of cells derived from a single progenitor cell.

Protease

The term protease as used herein is synonymous with peptidase or proteinase.

The protease for use in the present invention may be a subtilisin (E.C. 3.4.21.62) or a bacillolysin (E.C. 3.4.24.28) or an alkaline serine protease (E.C. 3.4.21.x) or a keratinase (E.C. 3.4.x.x).

Preferably the protease in accordance with the present invention is a subtilisin.

Suitable proteases include those of animal, vegetable or microbial origin. Chemically modified or protein engineered mutants are also suitable. The protease may be a serine protease or a metalloprotease, e.g., an alkaline microbial protease or a trypsin-like protease. Examples of alkaline proteases are subtilisins, especially those derived from *Bacillus* sp., e.g., subtilisin Novo, subtilisin Carlsberg, subtilisin 309 (see, e.g., U.S. Pat. No. 6,287,841), subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729 and WO 98/20115.

In one preferred embodiment the protease for use in the present invention may be one or more of the proteases in one or more of the commercial products below:

| Commercial product ® | Company | Protease type | Protease source |
|---|---|---|---|
| Avizyme 1100 | Danisco A/S | Subtilisin | Bacillus subtilis |
| Avizyme 1202 | Danisco A/S | Subtilisin | Bacillus subtilis |
| Avizyme 1302 | Danisco A/S | Subtilisin | Bacillus subtilis |
| Avizyme 1500 | Danisco A/S | Subtilisin | Bacillus subtilis |
| Avizyme 1505 | Danisco A/S | Subtilisin | Bacillus subtilis |
| Kemzyme Plus Dry | Kemin | Bacillolysin | Bacillus amyloliquefaciens |
| Kemzyme W dry | Kemin | Bacillolysin | Bacillus amyloliquefaciens |
| Natuzyme | Bioproton | Protease | Trichoderma longibrachiatum/ Trichoderma reesei |
| Porzyme 8300 | Danisco | Subtilisin | Bacillus subtilis |
| Ronozyme ProAct | DSM/Novozymes | Alkaline serine protease | Nocardiopsis prasina gene expressed in Bacillus licheniformis |
| Versazyme/Cibenza DP100 | Novus | Keratinase | Bacillus licheniformis |

In one embodiment the protease may be a protease from *B. subtilis*.

In one embodiment the protease may be a Nocardiopsis protease available from Novozymes A/S.

Preferably, the protease is present in the feedstuff in range of about 1000 U/kg to about 20,000 PU/kg feed, more preferably about 1500 PU/kg feed to about 10000 PU/kg feed, more preferably about 2000 PU/kg feed to about 6000 PU/kg feed.

In one embodiment the protease is present in the feedstuff at more than about 1000 PU/kg feed, suitably more than about 1500 PU/kg feed, suitably more than about 2000 PU/kg feed.

In one embodiment the protease is present in the feedstuff at less than about 20,000 PU/kg feed, suitably less than about 10000 PU/kg feed, suitably less than about 7000 PU/kg feed, suitably less than about 6000 PU/kg feed.

Preferably, the protease is present in the feed additive composition in range of about 200 PU/g to about 400,000 PU/g composition, more preferably about 300 PU/g composition to about 200,000 PU/g composition, and even more preferably about 5000 PU/g composition to about 100,000 PU/g composition, and even more preferably about 700 PU/g composition to about 70,000 PU/g composition, and even more preferably about 1000 PU/g composition to about 60,000 PU/g composition.

In one embodiment the protease is present in the feed additive composition at more than about 200 PU/g composition, suitably more than about 300 PU/g composition, suitably more than about 400 PU/g composition, suitably more than about 500 PU/g composition, suitably more than about 750 PU/g composition, suitably more than about 1000 PU/g composition.

In one embodiment the protease is present in the feed additive composition at less than about 400,000 PU/g composition, suitably less than about 200,000 PU/g composition, suitably less than about 100,000 PU/g composition, suitably less than about 80,000 PU/g composition, suitably less than about 70000 PU/g composition, suitably less than about 60000 PU/g composition.

It will be understood that one protease unit (PU) is the amount of enzyme that liberates from the substrate (0.6% casein solution) one microgram of phenolic compound (expressed as tyrosine equivalents) in one minute at pH 7.5 (40 mM $Na_2PO_4$/lactic acid buffer) and 40° C.

This may be referred to as the assay for determining 1 PU.

In one embodiment suitably the enzyme is classified using the E.C. classification above, and the E.C. classification designates an enzyme having that activity when tested in the assay taught herein for determining 1 PU.

Phytase

The phytase for use in the present invention may be classified a 6-phytase (classified as E.C. 3.1.3.26) or a 3-phytase (classified as E.C. 3.1.3.8).

In one embodiment the phytase may be a 6-phytase (E.C. 3.1.3.26).

In one preferred embodiment the phytase for use in the present invention may be one or more of the phytases in one or more of the commercial products below:

| Commercial product ® | Company | Phytase type | Phytase source |
|---|---|---|---|
| Finase | ABVista | 3-phytase | Trichoderma reesei |
| Finase EC | ABVista | 6-phytase | E. coli gene expressed in Trichoderma reesei |
| Natuphos | BASF | 3-phytase | Aspergillus Niger |
| Natuzyme | Bioproton | phytase (type not specified) | Trichoderma longibrachiatum/ Trichoderma reesei |
| OPTIPHOS ® | Huvepharma AD | 6-phytase | E. coli gene expressed in Pichia pastoris |
| Phytase sp1002 | DSM | 3-phytase | A consensus gene expressed in Hansenula polymorpha |
| Phyzyme XP | Danisco | 6-phytase | E. coli gene expressed in Schizosaccahomyces pombe |
| Quantum 2500D, 5000L | ABVista | 6-phytase | E. coli gene expressed in Pichia pastoris or Trichoderma |

-continued

| Commercial product ® | Company | Phytase type | Phytase source |
|---|---|---|---|
| Ronozyme Hi-Phos (M/L) | DSM/Novozymes | 6-phytase | *Citrobacter braakii* gene expressed in *Aspergillus oryzae* |
| Ronozyme NP | DSM/Novozymes | 6-phytase | *Peniphora lycii* gene expressed in *Aspergillus oryzae* |
| Ronozyme P | DSM/Novozymes | 6-phytase | *Peniphora lycii* gene expressed in *Aspergillus oryzae* |
| Rovabio PHY | Adisseo | 3-phytase | *Penicillium funiculosum* |

The term consensus gene as used herein means that the DNA vector used to transform the organism contains a synthetic phytase gene based on a consensus sequence, a URA gene from the non-pathogenic yeast *Saccharomyces cerevisiae* and the origin of replication of the *Escherichia coli* plasmid pBR322.

In one embodiment the phytase is a *Citrobacter* phytase derived from e.g. *Citrobacter freundii*, preferably *C. freundii* NCIMB 41247 and variants thereof e.g. as disclosed in WO2006/038062 (incorporated herein by reference) and WO2006/038128 (incorporated herein by reference), *Citrobacter braakii* YH-15 as disclosed in WO 2004/085638, *Citrobacter braakii* ATCC 51113 as disclosed in WO2006/037328 (incorporated herein by reference), as well as variants thereof e.g. as disclosed in WO2007/112739 (incorporated herein by reference) and WO2011/117396 (incorporated herein by reference), *Citrobacter amalonaticus*, preferably *Citrobacter amalonaticus* ATCC 25405 or *Citrobacter amalonaticus* ATCC 25407 as disclosed in WO2006037327 (incorporated herein by reference), *Citrobacter gillenii*, preferably *Citrobacter gillenii* DSM 13694 as disclosed in WO2006037327 (incorporated herein by reference), or *Citrobacter intermedius*, *Citrobacter koseri*, *Citrobacter murliniae*, *Citrobacter rodentium*, *Citrobacter sedlakii*, *Citrobacter werkmanii*, *Citrobacter youngae*, *Citrobacter* species polypeptides or variants thereof.

In one embodiment the phytase may be a phytase from *Citrobacter*, e.g. from *Citrobacter freundii*, such as the phytase enzyme(s) taught in WO2006/038128, which reference is incorporated herein by reference.

In preferred embodiments, the phytase is preferably *E. coli* phytase marketed under the name Phyzyme XP™ by Danisco A/S.

Alternatively the phytase may be a *Buttiauxella* phytase, e.g. a *Buttiauxella agrestis* phytase, for example, the phytase enzymes taught in WO 2006/043178, WO 2008/097619, WO2009/129489, WO2008/092901, PCT/US2009/41011 or PCT/IB2010/051804, all of which are incorporated herein by reference.

In one embodiment the phytase may be a phytase from *Hafnia*, e.g. from *Hafnia alvei*, such as the phytase enzyme(s) taught in US2008263688, which reference is incorporated herein by reference.

In one embodiment the phytase may be a phytase from *Aspergillus*, e.g. from *Apergillus orzyae*.

In one embodiment the phytase may be a phytase from *Penicillium*, e.g. from *Penicillium funiculosum*.

Preferably, the phytase is present in the feedstuff in range of about 200 FTU/kg to about 1000 FTU/kg feed, more preferably about 300 FTU/kg feed to about 750 FTU/kg feed, more preferably about 400 FTU/kg feed to about 500 FTU/kg feed.

In one embodiment the phytase is present in the feedstuff at more than about 200 FTU/kg feed, suitably more than about 300 FTU/kg feed, suitably more than about 400 FTU/kg feed.

In one embodiment the phytase is present in the feedstuff at less than about 1000 FTU/kg feed, suitably less than about 750 FTU/kg feed.

Preferably, the phytase is present in the feed additive composition in range of about 40 FTU/g to about 40,000 FTU/g composition, more preferably about 80 FTU/g composition to about 20,000 FTU/g composition, and even more preferably about 100 FTU/g composition to about 10,000 FTU/g composition, and even more preferably about 200 FTU/g composition to about 10,000 FTU/g composition.

In one embodiment the phytase is present in the feed additive composition at more than about 40 FTU/g composition, suitably more than about 60 FTU/g composition, suitably more than about 100 FTU/g composition, suitably more than about 150 FTU/g composition, suitably more than about 200 FTU/g composition.

In one embodiment the phytase is present in the feed additive composition at less than about 40,000 FTU/g composition, suitably less than about 20,000 FTU/g composition, suitably less than about 15,000 FTU/g composition, suitably less than about 10,000 FTU/g composition.

It will be understood that as used herein 1 FTU (phytase unit) is defined as the amount of enzyme required to release 1 µmol of inorganic orthophosphate from a substrate in one minute under the reaction conditions defined in the ISO 2009 phytase assay—A standard assay for determining phytase activity and 1 FTU can be found at *International Standard ISO/DIS* 30024: 1-17, 2009.

In one embodiment suitably the enzyme is classified using the E.C. classification above, and the E.C. classification designates an enzyme having that activity when tested in the assay taught herein for determining 1 FTU.

Advantages

The interaction of DFMs with enzymes is complicated and without wishing to be bound by theory, it is very surprising that we can see an improvement in the subject's resistance to necrotic enteritis, e.g. that we see a reduction in lesion scores for instance. Prior to the present invention the combination of DFMs and enzymes (e.g. as taught herein) had not been taught for this specific purpose.

One advantage of the present invention is that the feed additive composition according to the present invention can avoid the negative effects of necrotic enteritis or can be used for improving the subject's resistance to necrotic enteritis.

Without wishing to be bound by theory, phytase catalyzes the sequential hydrolysis of phytate, a principal storage form of phosphorus in cereals and legumes, to less phosphorylated myo-inositol derivatives with concomitant release of inorganic phosphate. Hydrolysis of phytate causes a reduction of endogenous losses of amino acids to the intestinal lumen. A reduction of endogenous amino acid losses in the intestine reduces the availability of nitrogen for bacterial growth, which helps the activity of DFMs on inhibition of *C. perfringens* and other pathogenic bacteria.

Without wishing to be bound in theory proteases cause non-specific hydrolysis of dietary protein yielding a variety of polypeptides in the intestinal lumen. Animals finalise protein hydrolysis and absorb such amino acids. However, in the case of enteric pathogenic challenges, pathogenic bacteria may take advantage of higher peptide availability in the lumen of jejunum and ileum. DFMs inhibit the growth of entero-pathogens by for example competing for N sources, as well as by direct inhibition.

In combination these enzymes and DFMs surprisingly provide a significant improvement on the pathogen reduction and/or resistance to necrotic enteritis compared with other DFM and enzyme combinations and/or DFMs alone and/or enzyme(s) alone.

Formulation of the DFM with the enzymes

The DFM and the enzymes may be formulated in any suitable way to ensure that the formulation comprises viable DFMs and active enzymes.

In one embodiment the DFM and enzymes may be formulated as a liquid, a dry powder or a granule.

The dry powder or granules may be prepared by means known to those skilled in the art, such as, in top-spray fluid bed coater, in a buttom spray Wurster or by drum granulation (e.g. High sheer granulation), extrusion, pan coating or in a microingredients mixer.

For some embodiments the DFM and/or the enzyme(s) may be coated, for example encapsulated. Suitably the DFM and enzymes may be formulated within the same coating or encapsulated within the same capsule. Alternatively one or both of the enzymes may be formulated within the same coating or encapsulated within the same capsule and the DFM could be formulated in a coating separate to the one or both of the enzymes. In some embodiments, such as where the DFM is capable of producing endospores, the DFM may be provided without any coating. In such circumstances, the DFM endospores may be simply admixed with one or both enzymes. In the latter case, the enzymes may be coated, e.g. encapsulated, for instance one or both of the enzymes may be coated, e.g. encapsulated. The enzymes may be encapsulated as mixtures (i.e. comprising one or both) of the enzymes or they may be encapsulated separately, e.g. as single enzymes. In one preferred embodiment both enzymes may be coated, e.g. encapsulated, together.

In one embodiment the coating protects the enzymes from heat and may be considered a thermoprotectant.

In one embodiment the feed additive composition is formulated to a dry powder or granules as described in WO2007/044968 (referred to as TPT granules) or WO1997/016076 or WO1992/012645 (each of which is incorporated herein by reference).

In one embodiment the feed additive composition may be formulated to a granule for feed compositions comprising: a core; an active agent; and at least one coating, the active agent of the granule retaining at least 50% activity, at least 60% activity, at least 70% activity, at least 80% activity after conditions selected from one or more of a) a feed pelleting process, b) a steam-heated feed pretreatment process, c) storage, d) storage as an ingredient in an unpelleted mixture, and e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

With regard to the granule at least one coating may comprise a moisture hydrating material that constitutes at least 55% w/w of the granule; and/or at least one coating may comprise two coatings. The two coatings may be a moisture hydrating coating and a moisture barrier coating. In some embodiments, the moisture hydrating coating may be between 25% and 60% w/w of the granule and the moisture barrier coating may be between 2% and 15% w/w of the granule. The moisture hydrating coating may be selected from inorganic salts, sucrose, starch, and maltodextrin and the moisture barrier coating may be selected from polymers, gums, whey and starch.

The granule may be produced using a feed pelleting process and the feed pretreatment process may be conducted between 70° C. and 95° C. for up to several minutes, such as between 85° C. and 95° C.

In one embodiment the feed additive composition may be formulated to a granule for animal feed comprising: a core; an active agent, the active agent of the granule retaining at least 80% activity after storage and after a steam-heated pelleting process where the granule is an ingredient; a moisture barrier coating; and a moisture hydrating coating that is at least 25% w/w of the granule, the granule having a water activity of less than 0.5 prior to the steam-heated pelleting process.

The granule may have a moisture barrier coating selected from polymers and gums and the moisture hydrating material may be an inorganic salt. The moisture hydrating coating may be between 25% and 45% w/w of the granule and the moisture harrier coating may be between 2% and 10% w/w of the granule.

The granule may be produced using a steam-heated pelleting process which may be conducted between 85° C. and 95° C. for up to several minutes.

In some embodiments the DFM (e.g. DFM endospores for example) may be diluted using a diluent, such as starch powder, lime stone or the like.

In one embodiment, the composition is in a liquid formulation suitable for consumption preferably such liquid consumption contains one or more of the following: a buffer, salt, sorbitol and/or glycerol.

In another embodiment the feed additive composition may be formulated by applying, e.g. spraying, the enzyme(s) onto a carrier substrate, such as ground wheat for example.

In one embodiment the feed additive composition according to the present invention may be formulated as a premix. By way of example only the premix may comprise one or more feed components, such as one or more minerals and/or one or more vitamins.

In one embodiment the DFM and/or enzymes for use in the present invention are formulated with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

Packaging

In one embodiment the feed additive composition and/or premix and/or feed or feedstuff according to the present invention is packaged.

In one preferred embodiment the feed additive composition and/or premix and/or feed or feedstuff is packaged in a bag, such as a paper bag.

In an alternative embodiment the feed additive composition and/or premix and/or feed or feedstuff may be sealed in a container. Any suitable container may be used.

Feed

The feed additive composition of the present invention may be used as—or in the preparation of—a feed.

The term "feed" is used synonymously herein with "feedstuff".

The feed may be in the form of a solution or as a solid—depending on the use and/or the mode of application and/or the mode of administration.

When used as—or in the preparation of—a feed—such as functional feed—the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

In a preferred embodiment the feed additive composition of the present invention is admixed with a feed component to form a feedstuff.

The term "feed component" as used herein means all or part of the feedstuff. Part of the feedstuff may mean one constituent of the feedstuff or more than one constituent of the feedstuff, e.g. 2 or 3 or 4. In one embodiment the term "feed component" encompasses a premix or premix constituents.

Preferably the feed may be a fodder, or a premix thereof, a compound feed, or a premix thereof. In one embodiment the feed additive composition according to the present invention may be admixed with a compound feed, a compound feed component or to a premix of a compound feed or to a fodder, a fodder component, or a premix of a fodder.

The term fodder as used herein means any food which is provided to an animal (rather than the animal having to forage for it themselves). Fodder encompasses plants that have been cut.

The term fodder includes hay, straw, silage, compressed and pelleted feeds, oils and mixed rations, and also sprouted grains and legumes.

Fodder may be obtained from one or more of the plants selected from: alfalfa (lucerne), barley, birdsfoot trefoil, brassicas, Chau moellier, kale, rapeseed (canola), rutabaga (swede), turnip, clover, alsike clover, red clover, subterranean clover, white clover, grass, false oat grass, fescue, Bermuda grass, brome, heath grass, meadow grasses (from naturally mixed grassland swards, orchard grass, rye grass, Timothy-grass, corn (maize), millet, oats, sorghum, soybeans, trees (pollard tree shoots for tree-hay), wheat, and legumes.

The term "compound feed" means a commercial feed in the form of a meal, a pellet, nuts, cake or a crumble. Compound feeds may be blended from various raw materials and additives. These blends are formulated according to the specific requirements of the target animal.

Compound feeds can be complete feeds that provide all the daily required nutrients, concentrates that provide a part of the ration (protein, energy) or supplements that only provide additional micronutrients, such as minerals and vitamins.

The main ingredients used in compound feed are the feed grains, which include corn, soybeans, sorghum, oats, and barley.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

Any feedstuff of the present invention may comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

A feedstuff of the present invention may contain at least 30%, at least 40%, at least 50% or at least 60% by weight corn and soybean meal or corn and full fat soy, or wheat meal or sunflower meal.

In addition or in the alternative, a feedstuff of the present invention may comprise at least one high fibre feed material and/or at least one by-product of the at least one high fibre feed material to provide a high fibre feedstuff. Examples of high fibre feed materials include: wheat, barley, rye, oats, by products from cereals, such as corn gluten meal, Distillers Dried Grain Solubles (DDGS), wheat bran, wheat middlings, wheat shorts, rice bran, rice hulls, oat hulls, palm kernel, and citrus pulp. Some protein sources may also be regarded as high fibre: protein obtained from sources such as sunflower, lupin, fava beans and cotton.

In the present invention the feed may be one or more of the following: a compound feed and premix, including pellets, nuts or (cattle) cake; a crop or crop residue: corn, soybeans, sorghum, oats, barley, corn stover, copra, straw, chaff, sugar beet waste; fish meal; freshly cut grass and other forage plants; meat and bone meal; molasses; oil cake and press cake; oligosaccharides; conserved forage plants: hay and silage; seaweed; seeds and grains, either whole or prepared by crushing, milling etc.; sprouted grains and legumes; yeast extract.

The term feed in the present invention also encompasses in some embodiments pet food. A pet food is plant or animal material intended for consumption by pets, such as dog food or cat food. Pet food, such as dog and cat food, may be either in a dry form, such as kibble for dogs, or wet canned form. Cat food may contain the amino acid taurine.

The term feed in the present invention also encompasses in some embodiments fish food. A fish food normally contains macro nutrients, trace elements and vitamins necessary to keep captive fish in good health. Fish food may be in the form of a flake, pellet or tablet. Pelleted forms, some of which sink rapidly, are often used for larger fish or bottom feeding species. Some fish foods also contain additives, such as beta carotene or sex hormones, to artificially enhance the color of ornamental fish.

The term feed in the present invention also encompasses in some embodiment bird food. Bird food includes food that is used both in birdfeeders and to feed pet birds. Typically bird food comprises of a variety of seeds, but may also encompass suet (beef or mutton fat).

As used herein the term "contacted" refers to the indirect or direct application of the composition of the present invention to the product (e.g. the feed). Examples of the application methods which may be used, include, but are not limited to, treating the product in a material comprising the feed additive composition, direct application by mixing the feed additive composition with the product, spraying the feed additive composition onto the product surface or dipping the product into a preparation of the feed additive composition.

In one embodiment the feed additive composition of the present invention is preferably admixed with the product (e.g. feedstuff). Alternatively, the feed additive composition may be included in the emulsion or raw ingredients of a feedstuff.

For some applications, it is important that the composition is made available on or to the surface of a product to be affected/treated. This allows the composition to impart one or more of the following favourable characteristics: performance benefits.

The feed additive compositions of the present invention may be applied to intersperse, coat and/or impregnate a product (e.g. feedstuff or raw ingredients of a feedstuff) with a controlled amount of DFM and enzymes.

The DFM and enzymes may be used simultaneously (e.g. when they are in admixture together or even when they are delivered by different routes) or sequentially (e.g. they may be delivered by different routes). In one embodiment preferably the DFM and enzymes are applied simultaneously. Preferably the DFM and enzymes are admixed prior to being delivered to a feedstuff or to a raw ingredient of a feedstuff.

The DFM in feed additive compositions according to the present invention—can be added in suitable concentrations—such as for example in concentrations in the final feed product which offer a daily dose of between about $2 \times 10^5$ CFU to about $2 \times 10^{11}$ CFU, suitably between about $2 \times 10^6$ to about $1 \times 10^{10}$, suitably between about $3.75 \times 10^7$ CFU to about $1 \times 10^{10}$ CFU.

Preferably, the feed additive composition of the present invention will be thermally stable to heat treatment up to about 70° C.; up to about 85° C.; or up to about 95° C. The heat treatment may be performed for up to about 1 minute; up to about 5 minutes; up to about 10 minutes; up to about 30 minutes; up to about 60 minutes. The term thermally stable means that at least about 75% of the enzyme components and/or DFM that were present/active in the additive before heating to the specified temperature are still present/active after it cools to room temperature. Preferably, at least about 80% of the enzyme components and/or DFM that were present and active in the additive before heating to the specified temperature are still present and active after it cools to room temperature.

In a particularly preferred embodiment the feed additive composition is homogenized to produce a powder.

In an alternative preferred embodiment, the feed additive composition is formulated to granules as described in WO2007/044968 (referred to as TPT granules) incorporated herein by reference.

In another preferred embodiment when the feed additive composition is formulated into granules the granules comprise a hydrated barrier salt coated over the protein core. The advantage of such salt coating is improved thermo-tolerance, improved storage stability and protection against other feed additives otherwise having adverse effect on the enzyme and/or DFM.

Preferably, the salt used for the salt coating has a water activity greater than 0.25 or constant humidity greater than 60% at 20° C.

Preferably, the salt coating comprises a $Na_2SO_4$.

The method of preparing a feed additive composition may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minutes, 2 minutes, 5 minutes, 10 minutes, 15 minutes, 30 minutes and 1 hour.

It will be understood that the feed additive composition of the present invention is suitable for addition to any appropriate feed material.

As used herein, the term feed material refers to the basic feed material to be consumed by an animal. It will be further understood that this may comprise, for example, at least one or more unprocessed grains, and/or processed plant and/or animal material such as soybean meal or bone meal.

As used herein, the term "feedstuff" refers to a feed material to which one or more feed additive compositions have been added.

It will be understood by the skilled person that different animals require different feedstuffs, and even the same animal may require different feedstuffs, depending upon the purpose for which the animal is reared.

Preferably, the feedstuff may comprise feed materials comprising maize or corn, wheat, barley, triticale, rye, rice, tapioca, sorghum, and/or any of the by-products, as well as protein rich components like soybean mean, rape seed meal, canola meal, cotton seed meal, sunflower seed mean, animal-by-product meals and mixtures thereof. More preferably, the feedstuff may comprise animal fats and/or vegetable oils.

Optionally, the feedstuff may also contain additional minerals such as, for example, calcium and/or additional vitamins.

Preferably, the feedstuff is a corn soybean meal mix.

In one embodiment, preferably the feed is not pet food.

In another aspect there is provided a method for producing a feedstuff. Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting—in particular by suitable techniques that may include at least the use of steam.

The feedstuff may be a feedstuff for a monogastric animal, such as poultry (for example, broiler, layer, broiler breeders, turkey, duck, geese, water fowl), swine (all age categories), a pet (for example dogs, cats) or fish, preferably the feedstuff is for poultry.

In one embodiment the feedstuff is not for a layer.

By way of example only a feedstuff for chickens, e.g. broiler chickens may be comprises of one or more of the ingredients listed in the table below, for example in the % ages given in the table below:

| Ingredients | Starter (%) | Finisher (%) |
|---|---|---|
| Maize | 46.2 | 46.7 |
| Wheat Middlings | 6.7 | 10.0 |
| Maize DDGS | 7.0 | 7.0 |
| Soyabean Meal 48% CP | 32.8 | 26.2 |
| An/Veg Fat blend | 3.0 | 5.8 |
| L-Lysine HCl | 0.3 | 0.3 |
| DL-methionine | 0.3 | 0.3 |
| L-threonine | 0.1 | 0.1 |
| Salt | 0.3 | 0.4 |
| Limestone | 1.1 | 1.1 |
| Dicalcium Phosphate | 1.2 | 1.2 |
| Poultry Vitamins and Micro-minerals | 0.3 | 0.3 |

By way of example only the diet specification for chickens, such as broiler chickens, may be as set out in the Table below:

| Diet specification | | |
|---|---|---|
| Crude Protein (%) | 23.00 | 20.40 |
| Metabolizable Energy Poultry (kcal/kg) | 2950 | 3100 |
| Calcium (%) | 0.85 | 0.85 |
| Available Phosphorus (%) | 0.38 | 0.38 |
| Sodium (%) | 0.18 | 0.19 |
| Dig. Lysine (%) | 1.21 | 1.07 |
| Dig. Methionine (%) | 0.62 | 0.57 |
| Dig. Methionine + Cysteine (%) | 0.86 | 0.78 |
| Dig. Threonine (%) | 0.76 | 0.68 |

By way of example only a feedstuff laying hens may be comprises of one or more of the ingredients listed in the table below, for example in the % ages given in the table below:

| Ingredient | Laying phase (%) |
|---|---|
| Maize | 10.0 |
| Wheat | 53.6 |
| Maize DDGS | 5.0 |
| Soybean Meal 48% CP | 14.9 |
| Wheat Middlings | 3.0 |
| Soybean Oil | 1.8 |
| L-Lysine HCl | 0.2 |
| DL-methionine | 0.2 |
| L-threonine | 0.1 |
| Salt | 0.3 |
| Dicalcium Phosphate | 1.6 |
| Limestone | 8.9 |
| Poultry Vitamins and Micro-minerals | 0.6 |

By way of example only the diet specification for laying hens may be as set out in the Table below:

| Diet specification | |
|---|---|
| Crude Protein (%) | 16.10 |
| Metabolizable Energy Poultry (kcal/kg) | 2700 |
| Lysine (%) | 0.85 |
| Methionine (%) | 0.42 |
| Methionine + Cysteine (%) | 0.71 |
| Threonine (%) | 0.60 |
| Calcium (%) | 3.85 |
| Available Phosphorus (%) | 0.42 |
| Sodium (%) | 0.16 |

By way of example only a feedstuff for turkeys may be comprises of one or more of the ingredients listed in the table below, for example in the % ages given in the table below:

| Ingredient | Phase 1 (%) | Phase 2 (%) | Phase 3 (%) | Phase 4 (%) |
|---|---|---|---|---|
| Wheat | 33.6 | 42.3 | 52.4 | 61.6 |
| Maize DDGS | 7.0 | 7.0 | 7.0 | 7.0 |
| Soyabean Meal 48% CP | 44.6 | 36.6 | 27.2 | 19.2 |
| Rapeseed Meal | 4.0 | 4.0 | 4.0 | 4.0 |
| Soyabean Oil | 4.4 | 4.2 | 3.9 | 3.6 |
| L-Lysine HCl | 0.5 | 0.5 | 0.4 | 0.4 |
| DL-methionine | 0.4 | 0.4 | 0.3 | 0.2 |
| L-threonine | 0.2 | 0.2 | 0.1 | 0.1 |
| Salt | 0.3 | 0.3 | 0.3 | 0.3 |
| Limestone | 1.0 | 1.1 | 1.1 | 1.0 |
| Dicalcium Phosphate | 3.5 | 3.0 | 2.7 | 2.0 |
| Poultry Vitamins and Micro-minerals | 0.4 | 0.4 | 0.4 | 0.4 |

By way of example only the diet specification for turkeys may be as set out in the Table below:

| Diet specification | | | | |
|---|---|---|---|---|
| Crude Protein (%) | 29.35 | 26.37 | 22.93 | 20.00 |
| Metabolizable Energy Poultry (kcal/kg) | 2.850 | 2.900 | 2.950 | 3.001 |
| Calcium (%) | 1.43 | 1.33 | 1.22 | 1.02 |
| Available Phosphorus (%) | 0.80 | 0.71 | 0.65 | 0.53 |
| Sodium (%) | 0.16 | 0.17 | 0.17 | 0.17 |
| Dig. Lysine (%) | 1.77 | 1.53 | 1.27 | 1.04 |
| Dig. Methionine (%) | 0.79 | 0.71 | 0.62 | 0.48 |
| Dig. Methionine + Cysteine (%) | 1.12 | 1.02 | 0.90 | 0.74 |
| Dig. Threonine (%) | 1.03 | 0.89 | 0.73 | 0.59 |

By way of example only a feedstuff for piglets may be comprises of one or more of the ingredients listed in the table below, for example in the % ages given in the table below:

| Ingredient | Phase 1 (%) | Phase 2 (%) |
|---|---|---|
| Maize | 20.0 | 7.0 |
| Wheat | 25.9 | 46.6 |
| Rye | 4.0 | 10.0 |
| Wheat middlings | 4.0 | 4.0 |
| Maize DDGS | 6.0 | 8.0 |
| Soyabean Meal 48% CP | 25.7 | 19.9 |
| Dried Whey | 10.0 | 0.0 |
| Soyabean Oil | 1.0 | 0.7 |
| L-Lysine HCl | 0.4 | 0.5 |
| DL-methionine | 0.2 | 0.2 |
| L-threonine | 0.1 | 0.2 |
| L-tryptophan | 0.03 | 0.04 |
| Limestone | 0.6 | 0.7 |
| Dicalcium Phosphate | 1.6 | 1.6 |
| Swine Vitamins and Micro-minerals | 0.2 | 0.2 |
| Salt | 0.2 | 0.4 |

By way of example only the diet specification for piglets may be as set out in the Table below:

| Diet specification | | |
|---|---|---|
| Crude Protein (%) | 21.50 | 20.00 |
| Swine Digestible Energy (kcal/kg) | 3380 | 3320 |
| Swine Net Energy (kcal/kg) | 2270 | 2230 |
| Calcium (%) | 0.80 | 0.75 |

-continued

| Diet specification | | |
|---|---|---|
| Digestible Phosphorus (%) | 0.40 | 0.35 |
| Sodium (%) | 0.20 | 0.20 |
| Dig. Lysine (%) | 1.23 | 1.14 |
| Dig. Methionine (%) | 0.49 | 0.44 |
| Dig. Methionine + Cysteine (%) | 0.74 | 0.68 |
| Dig. Threonine (%) | 0.80 | 0.74 |

By way of example only a feedstuff for grower/finisher pigs may be comprises of one or more of the ingredients listed in the table below, for example in the % ages given in the table below:

| Ingredient | Grower/Finisher (%) |
|---|---|
| Maize | 27.5 |
| Soyabean Meal 48% CP | 15.4 |
| Maize DDGS | 20.0 |
| Wheat bran | 11.1 |
| Rice bran | 12.0 |
| Canola seed meal | 10.0 |
| Limestone | 1.6 |
| Dicalcium phosphate | 0.01 |
| Salt | 0.4 |
| Swine Vitamins and Micro-minerals | 0.3 |
| Lysine-HCl | 0.2 |
| Vegetable oil | 0.5 |

By way of example only the diet specification for grower/finisher pigs may be as set out in the Table below:

| Diet specification | |
|---|---|
| Crude Protein (%) | 22.60 |
| Swine Metabolizable Energy (kcal/kg) | 3030 |
| Calcium (%) | 0.75 |
| Available Phosphorus (%) | 0.29 |
| Digestible Lysine (%) | 1.01 |
| Dig. Methionine + Cysteine (%) | 0.73 |
| Digestible Threonine (%) | 0.66 |

Forms

The feed additive composition of the present invention and other components and/or the feedstuff comprising same may be used in any suitable form.

The feed additive composition of the present invention may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

In some applications, DFM or feed additive compositions of the present invention may be mixed with feed or administered in the drinking water. In one embodiment the dosage range for inclusion into water is about $1\times10^3$ CFU/animal/day to about $1\times10^{10}$ CFU/animal/day, and more preferably about $1\times10^7$ CFU/animal/day.

Suitable examples of forms include one or more of: powders, pastes, boluses, pellets, tablets, pills, capsules, ovules, solutions or suspensions, which may contain flavouring or colouring agents, for immediate-, delayed-, modified-, sustained-, pulsed- or controlled-release applications.

By way of example, if the composition of the present invention is used in a solid, e.g. pelleted form, it may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Preferred excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

Non-hydroscopic whey is often used as a carrier for DFMs (particularly bacterial DFMs) and is a good medium to initiate growth.

Bacterial DFM containing pastes may be formulated with vegetable oil and inert gelling ingredients.

Fungal products may be formulated with grain by-products as carriers.

In one embodiment preferably the feed additive composition according to the present invention is not in the form of a microparticle system, such as the microparticle system taught in WO2005/123034.

Dosing

The DFM and/or feed additive composition according to the present invention may be designed for one-time dosing or may be designed for feeding on a daily basis.

The optimum amount of the composition (and each component therein) to be used in the combination of the present invention will depend on the product to be treated and/or the method of contacting the product with the composition and/or the intended use for the same.

The amount of DFM and enzymes used in the compositions should be a sufficient amount to be effective and to remain sufficiently effective in improving the performance of the animal fed feed products containing said composition. This length of time for effectiveness should extend up to at least the time of utilisation of the product (e.g. feed additive composition or feed containing same).

The ratio of DFM to each enzyme in the feed can be in the ranges given below:

DFM:phytase (CFU/FTU): In range from $5.0\times10^2$ CFU DFM: 1 FTU enzyme to $5.0\times10^9$ CFU: 1 FTU enzyme; preferably in the range from $7.5\times10^4$ CFU DFM: 1 FTU enzyme to $2.5\times10^7$ CFU:1 FTU enzyme.

DFM: protease (CFU/PU): In range from $5.0\times10^1$ CFU DFM: 1PU enzyme to $1.0\times10^9$ CFU: 1PU enzyme; preferably in the range from $1.25\times10^4$ CFU DFM: 1PU enzyme to $5.0\times10^6$ CFU: 1PU enzyme.

In one embodiment preferably the feedstuff comprises the following:
- a protease at at least 4000PU/kg of feed;
- a phytase at at least 500 FTU/kg of feed; and
- Envivo Pro (DFM) at at least 75,000 CFU/g to 150,000 CFU/g of feed.

In one embodiment preferably the feedstuff comprises the following:
- a protease at 4000PU/kg of feed;
- a phytase at 500 FTU/kg of feed; and
- Envivo Pro (DFM) at 75,000 CFU/g to 150,000 CFU/g of feed.

In one embodiment preferably the feedstuff comprises the following:
- a protease at 5000PU/kg of feed;
- a phytase at 625 FTU/kg of feed; and
- Envivo Pro (DFM) at 75,000 CFU/g to 150,000 CFU/g of feed.

In another embodiment the feedstuff comprises the following:
- a protease at 2000PU/kg of feed;
- a phytase at 500 FTU/kg of feed; and
- Envivo Pro (DFM) at 37,500 CFU/g to 75,000 CFU/g of feed.

In a preferred embodiment the feed additive composition comprises sufficient enzyme and DFMs to dose the feedstuff as follows:
- a protease at 4000PU/kg of feed;
- a phytase at 500 FTU/kg of feed; and
- Envivo Pro (DFM) at 75,000 CFU/g to 150,000 CFU/g of feed.

In a preferred embodiment the feed additive composition comprises sufficient enzyme and DFMs to dose the feedstuff as follows:
- a protease at 2000PU/kg of feed;
- a phytase at 500 FTU/kg of feed; and
- Envivo Pro (DFM) at 37,500 CFU/g to 75,000 CFU/g of feed.

Combination with Other Components

The DFM and enzyme(s) for use in the present invention may be used in combination with other components. Thus, the present invention also relates to combinations. The DFM in combination with a protease and phytase may be referred to herein as "the feed additive composition of the present invention".

The combination of the present invention comprises the feed additive composition of the present invention (or one or more of the constituents thereof) and another component which is suitable for animal consumption and is capable of providing a medical or physiological benefit to the consumer.

In one embodiment preferably the "another component" is not a further enzyme or a further DFM.

The components may be prebiotics. Prebiotics are typically non-digestible carbohydrate (oligo- or polysaccharides) or a sugar alcohol which is not degraded or absorbed in the upper digestive tract. Known prebiotics used in commercial products and useful in accordance with the present invention include inulin (fructo-oligosaccharide, or FOS) and transgalacto-oligosaccharides (GOS or TOS). Suitable prebiotics include palatinoseoligosaccharide, soybean oligosaccharide, alginate, xanthan, pectin, locust bean gum (LBG), inulin, guar gum, galacto-oligosaccharide (GOS), fructo-oligosaccharide (FOS), non-degradable starch, lactosaccharose, lactulose, lactitol, maltitol, maltodextrin, polydextrose (i.e. Litesse®), lactitol, lactosucrose, soybean oligosaccharides, palatinose, isomalto-oligosaccharides, gluco-oligosaccharides and xylo-oligosaccharides, pectin fragments, dietary fibres, mannan-oligosaccharides.

Dietary fibres may include non-starch polysaccharides, such as arabinoxylans, cellulose and many other plant components, such as resistant dextrins, inulin, lignin, waxes, chitins, pectins, beta-glucans and oligosaccharides.

In one embodiment the present invention relates to the combination of the feed additive composition according to the present invention (or one or more of the constituents thereof) with a prebiotic. In another embodiment the present invention relates to a feed additive composition comprising (or consisting essentially of or consisting of) a DFM in combination with a phytase, a protease and a prebiotic.

The prebiotic may be administered simultaneously with (e.g. in admixture together with or delivered simultaneously by the same or different routes) or sequentially to (e.g. by the same or different routes) the feed additive composition (or constituents thereof) according to the present invention.

Other components of the combinations of the present invention include polydextrose, such as Litesse®, and/or a maltodextrin and/or lactitol. These other components may be optionally added to the feed additive composition to assist the drying process and help the survival of DFM.

Further examples of other suitable components include one or more of: thickeners, gelling agents, emulsifiers, binders, crystal modifiers, sweeteners (including artificial sweeteners), rheology modifiers, stabilisers, anti-oxidants, dyes, enzymes, carriers, vehicles, excipients, diluents, lubricating agents, flavouring agents, colouring matter, suspending agents, disintegrants, granulation binders etc. These other components may be natural. These other components may be prepared by use of chemical and/or enzymatic techniques.

In one embodiment the DFM and/or enzymes may be encapsulated. In one embodiment the feed additive composition and/or DFM and/or enzymes is/are formulated as a dry powder or granule as described in WO2007/044968 (referred to as TPT granules)—reference incorporated herein by reference.

In one preferred embodiment the DFM and/or enzymes for use in the present invention may be used in combination with one or more lipids.

For example, the DFM and/or enzymes for use in the present invention may be used in combination with one or more lipid micelles. The lipid micelle may be a simple lipid micelle or a complex lipid micelle.

The lipid micelle may be an aggregate of orientated molecules of amphipathic substances, such as a lipid and/or an oil.

As used herein the term "thickener or gelling agent" refers to a product that prevents separation by slowing or preventing the movement of particles, either droplets of immiscible liquids, air or insoluble solids. Thickening occurs when individual hydrated molecules cause an increase in viscosity, slowing the separation. Gelation occurs when the hydrated molecules link to form a three-dimensional network that traps the particles, thereby immobilising them.

The term "stabiliser" as used here is defined as an ingredient or combination of ingredients that keeps a product (e.g. a feed product) from changing over time.

The term "emulsifier" as used herein refers to an ingredient (e.g. a feed ingredient) that prevents the separation of emulsions. Emulsions are two immiscible substances, one present in droplet form, contained within the other. Emulsions can consist of oil-in-water, where the droplet or dispersed phase is oil and the continuous phase is water; or water-in-oil, where the water becomes the dispersed phase and the continuous phase is oil. Foams, which are gas-in-liquid, and suspensions, which are solid-in-liquid, can also be stabilised through the use of emulsifiers.

As used herein the term "binder" refers to an ingredient (e.g. a feed ingredient) that binds the product together through a physical or chemical reaction. During "gelation" for instance, water is absorbed, providing a binding effect. However, binders can absorb other liquids, such as oils, holding them within the product. In the context of the present invention binders would typically be used in solid or low-moisture products for instance baking products: pastries, doughnuts, bread and others.

"Carriers" or "vehicles" mean materials suitable for administration of the DFM and/or enzymes and include any such material known in the art such as, for example, any liquid, gel, solvent, liquid diluent, solubilizer, or the like, which is non-toxic and which does not interact with any components of the composition in a deleterious manner.

The present invention provides a method for preparing a feed additive composition comprising admixing a DFM, a phytase and a protease with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

Examples of excipients include one or more of: microcrystalline cellulose and other celluloses, lactose, sodium citrate, calcium carbonate, dibasic calcium phosphate, glycine, starch, milk sugar and high molecular weight polyethylene glycols.

Examples of disintegrants include one or more of: starch (preferably corn, potato or tapioca starch), sodium starch glycollate, croscarmellose sodium and certain complex silicates.

Examples of granulation binders include one or more of: polyvinylpyrrolidone, hydroxypropylmethylcellulose (HPMC), hydroxypropylcellulose (HPC), sucrose, maltose, gelatin and acacia.

Examples of lubricating agents include one or more of: magnesium stearate, stearic acid, glyceryl behenate and talc.

Examples of diluents include one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes).

Preferably, when the feed additive composition of the present invention is admixed with another component(s), the DFM remains viable.

In one embodiment preferably the feed additive composition according to the present invention does not comprise chromium or organic chromium In one embodiment preferably the feed additive according to the present invention does not contain glucanase.

In one embodiment preferably the feed additive according to the present invention does not contain sorbic acid.

Concentrates

The DFMs for use in the present invention may be in the form of concentrates. Typically these concentrates comprise a substantially high concentration of a DFM.

Feed additive compositions according to the present invention may have a content of viable cells (colony forming units, CFUs) which is in the range of at least $10^4$ CFU/g (suitably including at least $10^5$ CFU/g, such as at least $10^6$ CFU/g, e.g. at least $10^7$ CFU/g, at least $10^8$ CFU/g) to about $10^{10}$ CFU/g (or even about $10^{11}$ CFU/g or about $10^{12}$ CFU/g).

When the DFM is in the form of a concentrate the feed additive compositions according to the present invention may have a content of viable cells in the range of at least $10^9$ CFU/g to about $10^{12}$ CFU/g, preferably at least $10^{10}$ CFU/g to about $10^{12}$ CFU/g.

Powders, granules and liquid compositions in the form of concentrates may be diluted with water or resuspended in water or other suitable diluents, for example, an appropriate growth medium such as milk or mineral or vegetable oils, to give compositions ready for use.

The DFM or feed additive composition of the present invention or the combinations of the present invention in the form of concentrates may be prepared according to methods known in the art.

In one aspect of the present invention the enzymes or feed is contacted by a composition in a concentrated form.

The compositions of the present invention may be spray-dried or freeze-dried by methods known in the art.

Typical processes for making particles using a spray drying process involve a solid material which is dissolved in an appropriate solvent (e.g. a culture of a DFM in a fermentation medium). Alternatively, the material can be suspended or emulsified in a non-solvent to form a suspension or emulsion. Other ingredients (as discussed above) or components such as anti-microbial agents, stabilising agents, dyes and agents assisting with the drying process may optionally be added at this stage.

The solution then is atomised to form a fine mist of droplets. The droplets immediately enter a drying chamber where they contact a drying gas. The solvent is evaporated from the droplets into the drying gas to solidify the droplets, thereby forming particles. The particles are then separated from the drying gas and collected.

Subject

The term "subject", as used herein, means an animal that is to be or has been administered with a feed additive composition according to the present invention or a feedstuff comprising said feed additive composition according to the present invention.

The term "subject", as used herein, means an animal. Preferably, the subject is a mammal, bird, fish or crustacean including for example livestock or a domesticated animal (e.g. a pet).

In one embodiment the "subject" is livestock.

The term "livestock", as used herein refers to any farmed animal. Preferably, livestock is one or more of cows or bulls (including calves), poultry, pigs (including piglets), poultry (including broilers, chickens and turkeys), birds, fish (including freshwater fish, such as salmon, cod, trout and carp, e.g. koi carp, and marine fish, such as sea bass), crustaceans (such as shrimps, mussels and scallops), horses (including race horses), sheep (including lambs).

In one embodiment the term livestock and/or poultry and/or chickens does not include egg layers.

In another embodiment the "subject" is a domesticated animal or pet or an animal maintained in a zoological environment.

The term "domesticated animal or pet or animal maintained in a zoological environment" as used herein refers to any relevant animal including canines (e.g. dogs), felines (e.g. cats), rodents (e.g. guinea pigs, rats, mice), birds, fish (including freshwater fish and marine fish), and horses.

In one embodiment the subject may be challenged by an enteric pathogen.

By way of example a subject may have one or more enteric pathogens present in its gut or digestive tract. For example a subject may have one or more enteric pathogens in its gut or digestive tract at a level which:

i) results in loss of performance of the animal and/or
ii) is at clinically relevant levels; or
iii) is at sub-clinical levels.

The enteric pathogen may be *Clostridium perfringens* for example.

Performance

As used herein, "animal performance" may be determined by the feed efficiency and/or weight gain of the animal and/or by the feed conversion ratio and/or by the digestibility of a nutrient in a feed (e.g. amino acid digestibility) and/or digestible energy or metabolizable energy in a feed and/or by nitrogen retention and/or by animals ability to avoid the negative effects of necrotic enteritis and/or by the immune response of the subject.

Preferably "animal performance" is determined by feed efficiency and/or weight gain of the animal and/or by the feed conversion ratio.

By "improved animal performance" it is meant that there is increased feed efficiency, and/or increased weight gain and/or reduced feed conversion ratio and/or improved digestibility of nutrients or energy in a feed and/or by improved nitrogen retention and/or by improved ability to avoid the negative effects of necrotic enteritis and/or by an improved immune response in the subject resulting from the use of feed additive composition of the present invention in feed in comparison to feed which does not comprise said feed additive composition.

Preferably, by "improved animal performance" it is meant that there is increased feed efficiency and/or increased weight gain and/or reduced feed conversion ratio.

As used herein, the term "feed efficiency" refers to the amount of weight gain in an animal that occurs when the animal is fed ad-libitum or a specified amount of food during a period of time.

By "increased feed efficiency" it is meant that the use of a feed additive composition according the present invention in feed results in an increased weight gain per unit of feed intake compared with an animal fed without said feed additive composition being present.

Feed Conversion Ratio (FCR)

As used herein, the term "feed conversion ratio" refers to the amount of feed fed to an animal to increase the weight of the animal by a specified amount.

An improved feed conversion ratio means a lower feed conversion ratio.

By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Nutrient Digestibility

Nutrient digestibility as used herein means the fraction of a nutrient that disappears from the gastro-intestinal tract or a specified segment of the gastro-intestinal tract, e.g. the small intestine. Nutrient digestibility may be measured as the difference between what is administered to the subject and what comes out in the faeces of the subject, or between what is administered to the subject and what remains in the digesta on a specified segment of the gastro intestinal tract, e.g. the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed.

Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

Nitrogen Retention

Nitrogen retention as used herein means as subject's ability to retain nitrogen from the diet as body mass. A negative nitrogen balance occurs when the excretion of nitrogen exceeds the daily intake and is often seen when the muscle is being lost. A positive nitrogen balance is often associated with muscle growth, particularly in growing animals.

Nitrogen retention may be measured as the difference between the intake of nitrogen and the excreted nitrogen by means of the total collection of excreta and urine during a period of time. It is understood that excreted nitrogen includes undigested protein from the feed, endogenous proteinaceous secretions, microbial protein, and urinary nitrogen.

Survival

The term survival as used herein means the number of subject remaining alive. The term "improved survival" may be another way of saying "reduced mortality".

Carcass Yield and Meat Yield

The term carcass yield as used herein means the amount of carcass as a proportion of the live body weight, after a commercial or experimental process of slaughter. The term carcass means the body of an animal that has been slaughtered for food, with the head, entrails, part of the limbs, and feathers or skin removed. The term meat yield as used herein means the amount of edible meat as a proportion of the live body weight, or the amount of a specified meat cut as a proportion of the live body weight.

Weight gain

The present invention further provides a method of increasing weight gain in a subject, e.g. poultry or swine, comprising feeding said subject a feedstuff comprising a feed additive composition according to the present invention.

An "increased weight gain" refers to an animal having increased body weight on being fed feed comprising a feed additive composition compared with an animal being fed a feed without said feed additive composition being present.

Necrotic Enteritis

Necrotic enteritis is an acute or chronic enterotoxemia seen in chickens, turkeys and ducks worldwide, caused by *Clostridium perfringens*. Necrotic enteritis is often characterised by a fibrino-necrotic enteritis, usually of the mid-small intestine. Mortality may be 5-50%, usually around 10%. Infection occurs by faecal-oral transmission. Spores of the causative organism are highly resistant. Predisposing factors include coccidiosis/coccidiasis, diet (high protein), in ducks possibly heavy strains, high viscosity diets (often associated with high rye and wheat inclusions in the diet), contaminated feed and/or water, other debilitating diseases.

The present invention relates to increasing the subject's resistance to necrotic enteritis. In other words, the present invention relates to avoiding or reducing the negative effect of necrotic enteritis.

The term "resistance to" as used herein may encompasses the term "tolerance of". Therefore in one embodiment the subject may not be resistant to necrotic enteritis but the subject may be able to tolerate the necrotic enteritis, i.e. without negative effects on performance of the subject.

In one embodiment the present invention relates to a feed additive composition according to the present invention for treating or preventing necrotic enteritis in a subject. Typically the subject will be one which has been or will be challenged with *Clostridium perfringens* and/or *Eimeria* species. Such challenge may come from the environment or the application of live microorganisms in the feed or drinking water, e.g. when live coccidia vaccines are used.

In another embodiment the present invention relates to a feed additive composition for preventing and/or treating coccidiosis in a subject.

The present invention yet further provides a method of preventing and/or treating necrotic enteritis and/or coccidiosis wherein an effective amount of a feed additive composition according to the present invention is administered to a subject.

Immune Response

Immune response as used herein means one of the multiple ways in which DFMs modulate the immune system of animals, including increased antibody production, up-regulation of cell mediated immunity, up-regulation of pro-inflammatory cytokines, and augmented toll-like receptor signalling. It is understood that immuno-stimulation of the gastro intestinal tract by DFMs may be advantageous to protect the host against disease, and that immuno-suppression of the gastro intestinal tract may be advantageous to the host because less nutrients and energy are used to support the immune function.

Preferably the immune response is a cellular immune response.

Preferably immune response is measure by looking at immune markers.

Pathogenic Bacteria

The term pathogenic bacteria as used herein means for example toxigenic clostridia species, e.g. *Clostridium perfringens* and/or *E. coli* and/or *Salmonella* spp and/or *Campylobacter* spp. In one embodiment the pathogenic bacteria may be Avian pathogenic *E. coli* species.

The present invention may reduce populations of pathogenic bacteria in the gastrointestinal tract of a subject.

Nutrient Excretion

In one embodiment the present invention relates to reducing nutrient excretion in manure. This has positive effects on reducing environmental hazards. For example, in a preferred embodiment the present invention relates to reducing nitrogen and/or phosphorus content in the subject's manure. This, therefore, reduces the amount of nitrogen and/or phosphorus in the environment, which can be beneficial.

Probiotic

For some applications, it is believed that the DFM in the composition of the present invention can exert a probiotic culture effect. It is also within the scope of the present invention to add to the composition of the present invention further probiotic and/or prebiotics.

Here, a prebiotic is:

"a non-digestible food ingredient that beneficially affects the host by selectively stimulating the growth and/or the activity of one or a limited number of beneficial bacteria".

The term "probiotic culture" as used herein defines live microorganisms (including bacteria or yeasts for example) which, when for example ingested or locally applied in sufficient numbers, beneficially affects the host organism, i.e. by conferring one or more demonstrable health benefits on the host organism. Probiotics may improve the microbial balance in one or more mucosal surfaces. For example, the mucosal surface may be the intestine, the urinary tract, the respiratory tract or the skin. The term "probiotic" as used herein also encompasses live microorganisms that can stimulate the beneficial branches of the immune system and at the same time decrease the inflammatory reactions in a mucosal surface, for example the gut.

Whilst there are no lower or upper limits for probiotic intake, it has been suggested that at least $10^6$-$10^{12}$, preferably at least $10^6$-$10^{10}$, preferably $10^8$-$10^9$, cfu as a daily dose will be effective to achieve the beneficial health effects in a subject.

Isolated

In one aspect, suitably the enzyme or DFM used in the present invention may be in an isolated form. The term "isolated" means that the enzyme or DFM is at least substantially free from at least one other component with which the enzyme or DFM is naturally associated in nature and as found in nature. The enzyme or DFM of the present invention may be provided in a form that is substantially free of one or more contaminants with which the substance might otherwise be associated. Thus, for example it may be substantially free of one or more potentially contaminating polypeptides and/or nucleic acid molecules.

Purified

In one aspect, preferably the enzyme and/or DFM according to the present invention is in a purified form. The term "purified" means that the enzyme and/or DFM is present at a high level. The enzyme and/or DFM is desirably the predominant component present in a composition. Preferably, it is present at a level of at least about 90%, or at least about 95% or at least about 98%, said level being determined on a dry weight/dry weight basis with respect to the total composition under consideration.

It is envisaged within the scope of the present invention that the embodiments of the invention can be combined such that combinations of any of the features described herein are included within the scope of the present invention. In particular, it is envisaged within the scope of the present invention that any of the therapeutic effects of the bacteria may be exhibited concomitantly.

EXAMPLES

Example 1

Materials and Methods

Three thousand six hundred one-day-old Cobb male chicks are purchased from a commercial hatchery. At study initiation, fifty males are allocated to each treatment pen by blocks. The study consisted of the following treatments (Table 1):

TABLE 1

Experimental design of Example 1.

| Treatment | Clostridium perfringens Challenge | Phytase[1] | Additional enzyme[2] | DFM[3] |
|---|---|---|---|---|
| 1 | No | 500 FTU/kg | None | None |
| 2 | Yes | 500 FTU/kg | None | None |
| 3 | Yes | 500 FTU/kg | Protease (5000 u/kg) | None |
| 4 | Yes | 500 FTU/kg | None | Enviva Pro (7.5 × 10$^4$ CFU/g) |
| 5 | Yes | 500 FTU/kg | Protease (5000 u/kg) | Enviva Pro (7.5 × 10$^4$ CFU/g) |

[1]Phytase from *E. coli*.
[2]protease from *Bacillus subtilis*.
[3]Enviva Pro ® is combination of *Bacillus subtilis* strains Bs2084, LSSAO1 and 15AP4, provided by Danisco A/S.

Bird weights by pen were recorded at study initiation, 23 d, 35 d, and termination (42d). The pen was the unit of measure. Broiler diets were fed as crumbles (starter) or pellets (grower and finisher). Diets met or exceeded NRC standards (Table 2). The mixer was flushed to prevent cross contamination of diets. All treatment feeds were mixed using a Davis S-20 mixer and pelleted using a California Pellet Mill (cold pellet temperature 65-70 C). Samples were collected from each treatment diet from the beginning, middle, and end of each batch and blended together to confirm enzyme activities and Enviva Pro presence in feed.

TABLE 2

Experimental diet composition of Example 1.

| Ingredient (%) | Starter | Grower | Finisher |
|---|---|---|---|
| Maize | 53.62 | 57.87 | 59.82 |
| Maize DDGS | 10.00 | 10.00 | 10.00 |
| Soybean Meal 49% CP | 26.93 | 23.97 | 21.36 |
| Ampro 55 | 5.00 | 5.00 | 5.00 |
| Soy oil | 2.07 | 0.91 | 1.74 |
| Lysine | 0.24 | 0.24 | 0.24 |
| DL-methionine | 0.21 | 0.19 | 0.18 |
| L-threonine | 0.01 | 0.01 | 0.01 |
| Salt | 0.30 | 0.34 | 0.35 |
| Limestone | 1.04 | 1.07 | 0.94 |
| Dicalcium phosphate | 0.26 | 0.11 | 0.02 |
| Vitamin and trace mineral premix | 0.33 | 0.33 | 0.33 |
| Calculated Nutrient Composition (%) | | | |
| CP | 22.60 | 21.50 | 20.39 |
| Energy, kcal/kg | 3060 | 3025 | 3100 |
| Digestible lysine | 1.36 | 1.26 | 1.21 |
| Digestible methionine | 0.58 | 0.61 | 0.53 |
| Digestible threonine | 0.83 | 0.83 | 0.80 |

Birds receive feed ad-libitum appropriate to the treatment from Day 0 to 42. Enzymes and Enviva Pro are provided by Danisco in the appropriate mixtures and levels for all experimental treatments. All diets contained 500 FTU of *E. coli* phytase in the background. The pens are arranged within the facility to prevent direct contact in order to avoid contamination. A change from starter to grower occurred on Day 21. Grower diet is replaced with the finisher diet on Day 35. At each feed change, feeders are removed from pens by block, weighed back, emptied, and refilled with the appropriate treatment diet. On the final day of the study feed is weighed. Pens are checked daily for mortality. When a bird is culled or found dead, the date and removal weight (kg) are recorded. A gross necropsy is performed on all dead or culled birds to determine the sex and probable cause of death. Signs of Necrotic Enteritis are noted.

All pens had approximately 4 inches of built up litter with a coating of fresh pine shavings.

All birds are spray vaccinated prior to placement into pens with a commercial coccidiosis vaccine (Coccivac-B). On Days 18, 19, and 20 all birds, except Treatment 1, are dosed with a broth culture of *C. perfringens*. A field isolate of *C. perfringens* known to cause NE and originating from a commercial broiler operation is utilized as the challenge organism. Fresh inoculum is used each day. The titration levels are approximately $1.0 \times 10^{8-9}$. Each pen receive the same amount of inoculum. The inoculum is administered by mixing into the feed found in the base of the tube feeder. On Day 21, five birds from each pen are selected, euthanized, group weighed, and examined for the degree of presence of Necrotic Enteritis lesions. The scoring was based on a 0 to 3 score, with 0 being normal and 3 being the most severe (0=none, 1=mild, 2=moderate, 3=marked/severe; Hofacre et al., 2003 J. Appl. Poult. Res. 12:60-64). No concomitant drug therapy is used during the study.

Means were separated using pair wise t-tests. Significant differences are considered at P<0.05. Pens are used as the experimental unit.

Results

FIG. 1 shows the necrotic enteritis lesion scores of broiler chickens in a necrotic enteritis challenge model, based on a 0 to 3 score system. Pooled SEM=0.15

As expected, the challenged control treatment increased lesion scores compared to the unchallenged control treatment. Addition of DFMs in a combination of a protease and phytase surprisingly reduce lesion scores compared to all other treatments.

Figure 2:
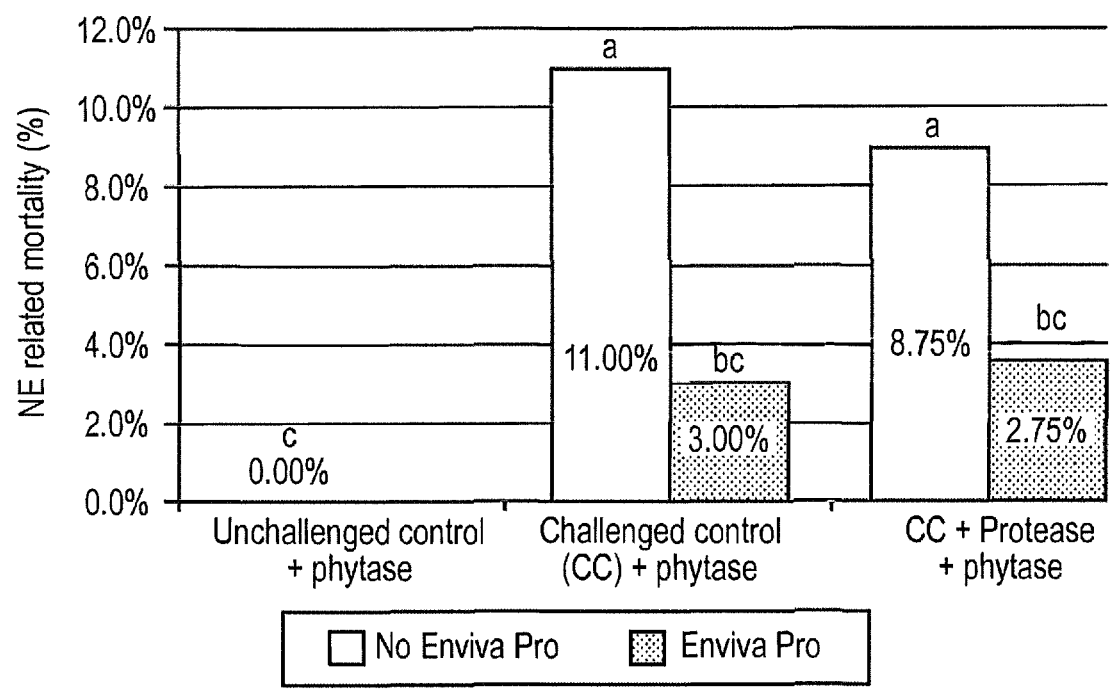
FIG. 2 shows percentage of morality related to necrotic enteritis (NE) lesions from 20 to 42 d of age. A combination of DFM (Enviva Pro® available from Danisco A/S) with a combination of a protease (e.g. *Bacillus subtilis* protease) and a phytase (e.g. 500 FTU/kg of Phyzyme XP (an *E. coli* phytase) available from Danisco A/S) significantly improved (reduced) NE mortality.

FIG. 2 shows percentage of morality related to necrotic enteritis (NE) lesions from 20 to 42 d of age.

The challenged control treatment increased NE related mortality compared to the unchallenged control treatment. Addition of DFMs reduced NE mortality compared to the challenged control, with and without protease+phytase.

Figure 3:
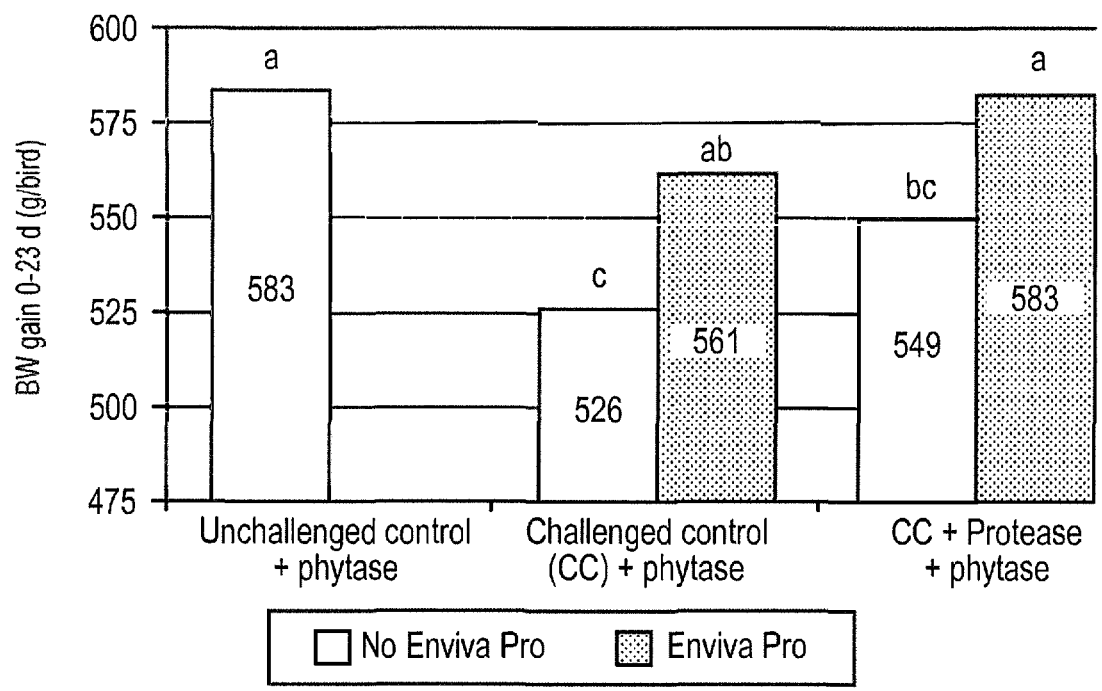
FIG. 3 shows the body weight gain of broiler chickens from 0 to 23 d in a necrotic enteritis challenge model. A combination of (Enviva Pro® available from Danisco A/S) with a combination of a protease (e.g. *Bacillus subtilis* protease) and a phytase (e.g. 500 FTU/kg of Phyzyme XP (an *E. coli* phytase) available from Danisco A/S) significantly improved Body weight gain (BW gain) in broiler chickens challenged with *Clostridium perfringens* compared with the challenged control.

FIG. 3 shows the body weight gain of broiler chickens from 0 to 23 d in a necrotic enteritis challenge model. Pooled SEM=28.6

FIG. 3 shows that a combination of the DFM (Enviva Pro®) with a combination of a protease and a phytase significantly improves body weight gain (BW gain) in broiler chickens challenged with *Clostridium perfringens* compared with the challenged control. The data shows that the DFM in combination with the protease and phytase surprisingly improved total BW gain to the level of the unchallenged control+phytase.

Figure 4:
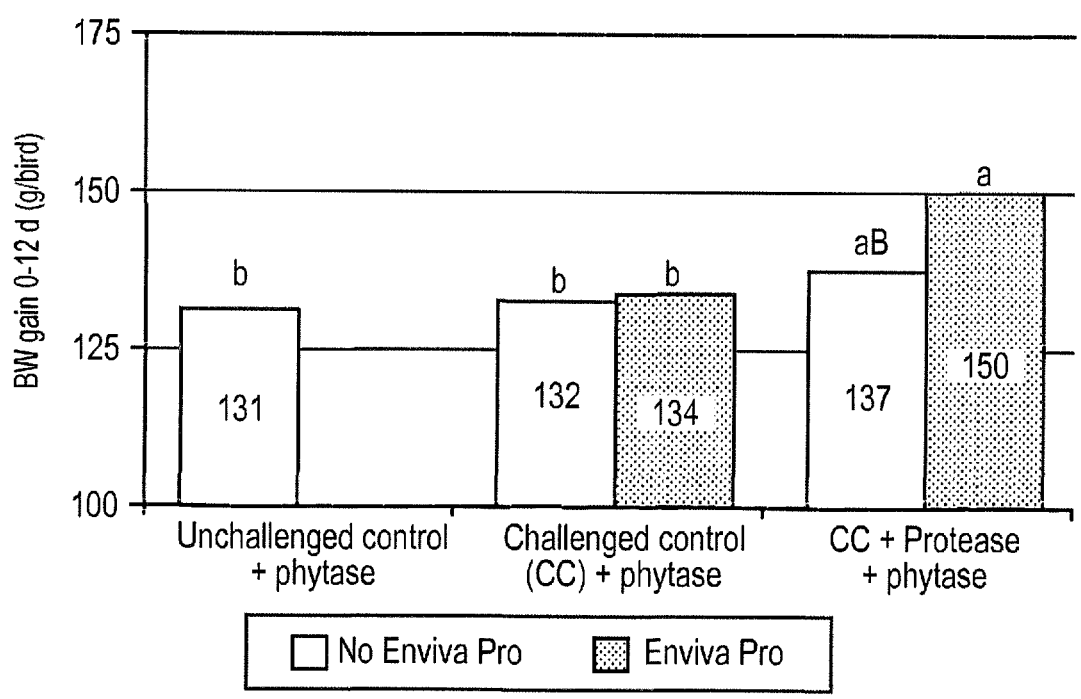
FIG. 4 shows the body weight gain of broiler chickens from 0-12 days in necrotic enteritis challenge model. Pooled SEM=4.86.

FIG. 4 shows the body weight gain of broiler chickens from 0 to 12 days in a necrotic enteritis challenge model. Pooled SEM=4.86.

Figure 5:
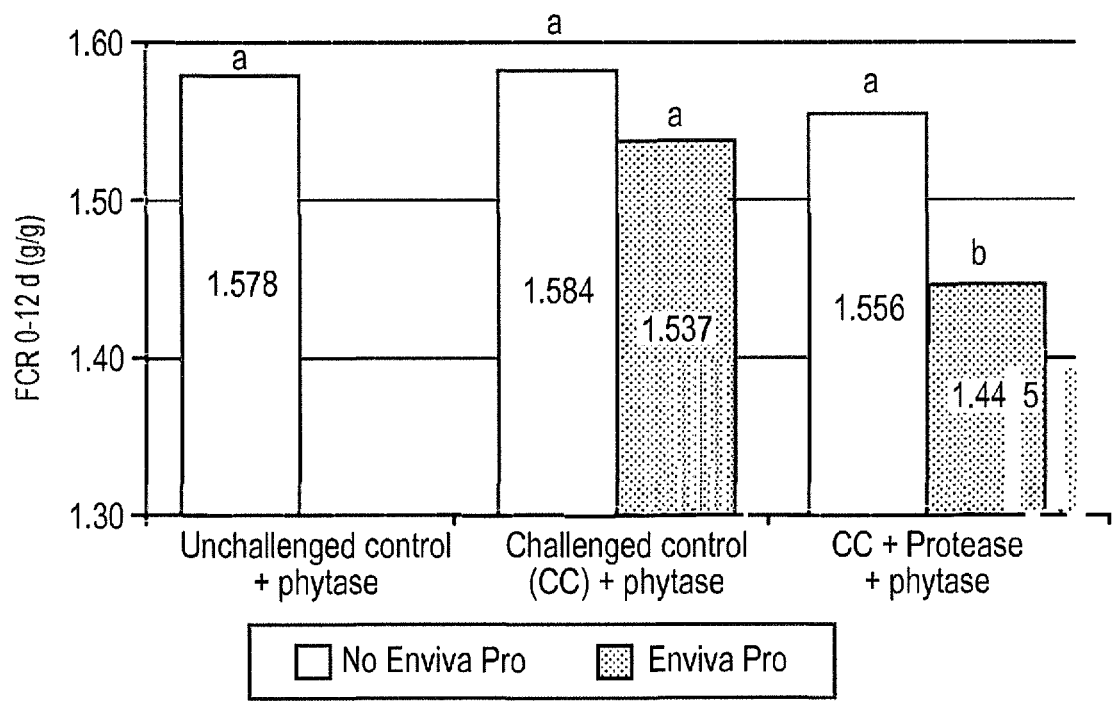
FIG. 5 shows the feed conversion ratio of broiler chickens in a necrotic enteritis challenge model. Pooled SEM=0.026.

FIG. 5 shows the feed conversion ratio 0-12 d of broiler chickens in a necrotic enteritis challenge model. Pooled SEM=0.026

The combination of Enviva Pro (DFM) with a protease and phytase significantly improved (reduced) FCR (g BW gain/g feed intake) of broilers from 0 to 12 d compared to the challenged control, and enzymes by themselves and the other treatments.

Figure 6:
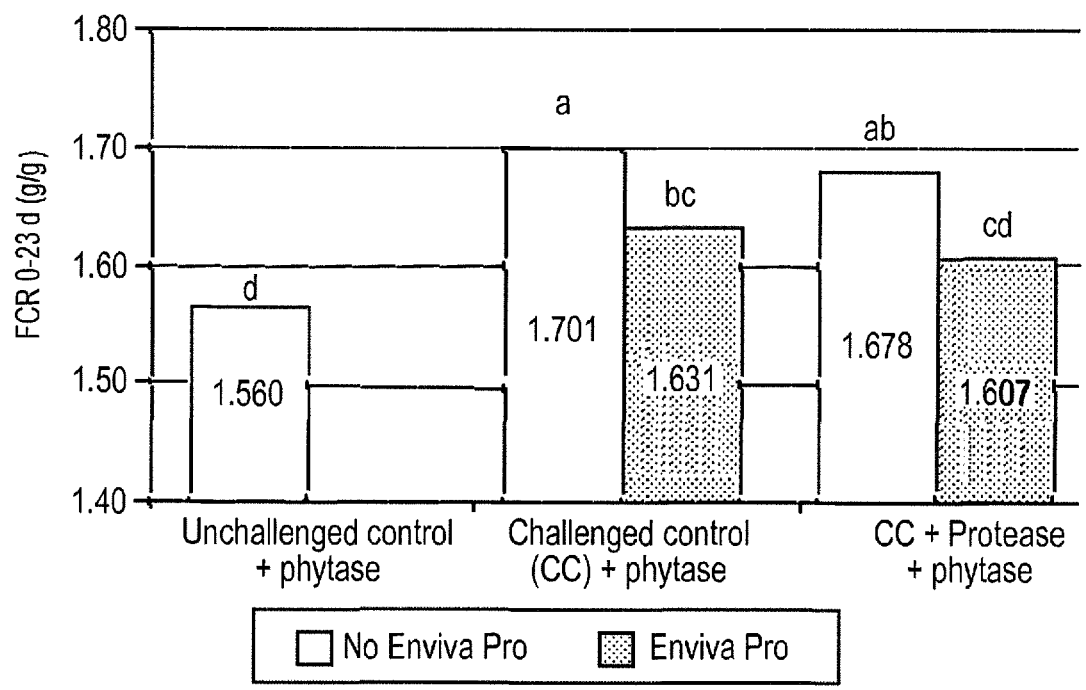
FIG. 6 shows the feed conversion ratio 0-23 d of broiler chickens in a necrotic enteritis challenge model. Pooled SEM=0.022.

FIG. 6 shows the feed conversion ratio (0-23 d) of broiler chickens in a necrotic enteritis challenge model. Pooled SEM=0.022

The combination of Enviva Pro (DFM) with a protease and phytase significantly improved (reduced) FCR (g BW gain/g feed intake) of broilers 0 to 23 days compared to the challenged control, and enzymes by themselves and the other treatments.

Example 2

Materials and Methods

One digestibility trial with broiler chickens is conducted to determine the effects of protease and DFMs treatments on top of phytase on nutrient utilisation. The cages are housed in environmentally controlled rooms. The birds receive 20-hour fluorescent illumination and, are allowed free access to the diets and water. On day 1, a broiler live coccidiosis vaccine is given to all chicks orally. The study consists of the following treatments (Table 3).

TABLE 3

Experimental design of Example 2.

| Treatment | Phytase[1] | Protease | DFM[2] |
|---|---|---|---|
| 1 | 500 FTU/kg | None | None |
| 2 | 500 FTU/kg | Protease 1[3] (5000 u/kg) | None |
| 3 | 500 FTU/kg | Protease 1[3] (5000 u/kg) | None |
| 4 | 500 FTU/kg | Protease 2[4] (15000 u/kg) | None |
| 5 | 500 FTU/kg | None | Enviva Pro (1.5 × 10$^5$ CFU/g) |
| 6 | 500 FTU/kg | Protease 1[3] (5000 u/kg) | Enviva Pro (1.5 × 10$^5$ CFU/g) |
| 7 | 500 FTU/kg | Protease 1[3] (5000 u/kg) | Enviva Pro (1.5 × 10$^5$ CFU/g) |
| 8 | 500 FTU/kg | Protease 2[4] (15000 u/kg) | Enviva Pro (1.5 × 10$^5$ CFU/g) |

[1]Phytase from *E. coli* provided by Danisco A/S.
[2]Enviva Pro ® is combination of *Bacillus subtilis* strains Bs2084, LSSAO1 and 15AP4, provided by Danisco A/S.
[3]Protease from *Bacillus subtilis* provided by Danisco A/S.
[4]Protease from *Bacillus licheniformis*.

A total of 512 birds are individually weighed and assigned on the basis of body weight to 64 cages (8 birds/cage). The 8 dietary treatments are then randomly assigned to 8 cages each. Birds receive starter feed ad-libitum appropriate to the treatment from 0 to 21 days. Enzymes and Enviva Pro are provided by Danisco in the appropriate mixtures and levels for all experimental treatments. All diets contain 500 FTU of *E. coli* phytase in the background. The pens are arranged within the facility to prevent direct contact in order to avoid contamination. Birds are fed starter diets (Table 4) in mash form throughout the experiment.

TABLE 4

Experimental diet composition of Example 2.

| Ingredient (%) | Starter |
|---|---|
| Maize | 50.11 |
| Maize DDGS | 10.00 |
| Soyabean Meal 48% CP | 28.83 |
| Canola Meal | 5.00 |
| An/Veg Fat blend | 2.16 |
| L-Lysine HCl | 0.33 |
| DL-methionine | 0.28 |
| L-threonine | 0.12 |
| Inert marker (TiO2) | 0.30 |
| Salt | 0.33 |
| Limestone | 1.09 |
| Dicalcium Phosphate | 1.15 |
| Poultry vitamins and micro-minerals | 0.30 |
| Calculated Nutrient Composition (%) | |
| CP | 23.00 |
| ME, kcal/kg | 2950 |
| Calcium | 0.85 |
| Available phosphorus | 0.38 |
| Sodium | 0.18 |
| Digestible lysine | 1.21 |
| Digestible methionine | 0.62 |
| Digestible TSAA | 0.86 |
| Digestible threonine | 0.76 |

On d 21, 8 birds per cage are euthanized by cervical dislocation and contents of the lower ileum are expressed by gentle flushing with distilled water. Digesta from birds within a cage are pooled, resulting in 8 samples per dietary treatment. The digesta samples are frozen immediately after collection, lyophilised and processed. Digesta samples and diets are analysed for Ti, DM, GE, starch, fat, N, amino acids, excluding tryptophan, and soluble and insoluble non-starch polysaccharides (NSPs) as per standard procedures. Calculation of ileal digestibility coefficients is performed as reported by Ravindran et al. (2005), based on the concentration of indigestible Ti.

Representative samples of excreta per cage are collected over four consecutive days (from day 17 to 20) for the determination of nitrogen-corrected apparent metabolizable energy (AMEn) and Nitrogen retention, based on the concentration of Ti in feed and excreta samples. Daily excreta collections are pooled within a cage, mixed in a blender and sub-sampled. Each sub sample was lyophilized, ground to pass through a 0.5 mm sieve and stored in airtight plastic containers at −4 C pending analysis. Processed samples are analysed for Ti, DM, GE, N, and soluble and insoluble NSPs as per standard procedures.

Means are separated using pair wise t-tests. Significant differences are considered at P<0.05. Cages are used as the experimental unit.

Results

Preliminary results show that the combination of protease, phytase and DFMs exhibits a greater ileal digestibility of energy, N, amino acids, starch, fat, and/or soluble and insoluble NSPs compared to the negative control treatment+phytase and protease+phytase and/or DFMs+phytase. The combination of protease and DFMs on top of phytase exhibits a greater AME, nitrogen retention, and total tract disappearance of soluble and insoluble NSPs compared to the negative control treatment+phytase and protease+phytase and/or DFMs+phytase. The dose response of protease to these parameters exhibits a greater slope in treatments containing DFMs compared to treatments without DFMs.

Example 3

Materials and Methods

One digestibility trial with broiler chickens is conducted to determine the effects of phytase+protease and DFMs treatments on nutrient utilisation. The cages are housed in environmentally controlled rooms. The birds receive 20-hour fluorescent illumination and, allowed free access to the diets and water. On day 1, a broiler live coccidiosis vaccine is given to all chicks in a spray cabinet. The study consists of the following treatments (Table 5).

TABLE 5

Experimental design of Example 3.

| Treatment | Phytase[1] | Protease[2] | DFM |
|---|---|---|---|
| 1 | None | None | |
| 2 | 500 FTU/kg | 5000 u/kg | |
| 3 | None | None | Enviva Pro[3] ($1.5 \times 10^5$ CFU/g) |
| 4 | 500 FTU/kg | 5000 u/kg | Enviva Pro[3] ($1.5 \times 10^5$ CFU/g) |
| 5 | None | None | Calsporin[4] ($5.0 \times 10^6$ CFU/g) |
| 6 | 500 FTU/kg | 5000 u/kg | Calsporin[4] ($5.0 \times 10^6$ CFU/g) |
| 7 | None | None | Gallipro Tect[5] ($8.0 \times 10^5$ CFU/g) |
| 8 | 500 FTU/kg | 5000 u/kg | Gallipro Tect[5] ($8.0 \times 10^5$ CFU/g) |

[1]Phytase from *E. coli*.
[2]Protease from *Bacillus subtilis* provided by Danisco A/S.
[3]Enviva Pro ® is combination of *Bacillus subtilis* strains Bs2084, LSSAO1 and 15AP4, provided by Danisco A/S.
[4]Calsporin is a DFM product containing *Bacillus subtilis* Strain C3102.
[5]Gallipro Tect is a DFM product containing *Bacillus licheniformis* DSM17236.

A total of 384 birds are individually weighed and assigned on the basis of body weight to 64 cages (6 birds/cage). The 8 dietary treatments are then randomly assigned to 8 cages each. Birds receive starter feed ad-libitum appropriate to the treatment from 0 to 21 days. Enzymes and Enviva Pro are provided by Danisco in the appropriate mixtures and levels for all experimental treatments. The pens are arranged within the facility to prevent direct contact in order to avoid contamination. Birds were fed starter diets (Table 6) in mash form throughout the experiment.

TABLE 6

Experimental diet composition of Example 3.

| Ingredient (%) | Starter |
|---|---|
| Maize | 50.11 |
| Maize DDGS | 10.00 |
| Soyabean Meal 48% CP | 28.83 |
| Canola Meal | 5.00 |
| An/Veg Fat blend | 2.16 |
| L-Lysine HCl | 0.33 |
| DL-methionine | 0.28 |
| L-threonine | 0.12 |
| Inert marker (TiO$_2$) | 0.30 |
| Salt | 0.33 |
| Limestone | 1.09 |
| Dicalcium Phosphate | 1.15 |
| Poultry vitamins and micro-minerals | 0.30 |
| Calculated Nutrient Composition (%) | |
| CP | 23.00 |
| ME, kcal/kg | 2950 |
| Calcium | 0.85 |
| Available phosphorus | 0.38 |
| Sodium | 0.18 |
| Digestible lysine | 1.21 |
| Digestible methionine | 0.62 |
| Digestible TSAA | 0.86 |
| Digestible threonine | 0.76 |

On d 21, 6 birds per cage are euthanized by $CO_2$ asphyxiation and contents of the lower ileum are expressed by gentle flushing with distilled water. Digesta from birds within a cage are pooled, resulting in 8 samples per dietary treatment. The digesta samples are frozen immediately after collection, lyophilised and processed. Digesta samples and diets are analysed for Ti, DM, GE, starch, fat, N, and soluble and insoluble NSPs as per standard procedures. Calculation of ileal digestibility coefficients is performed as reported by Ravindran et al. (2005), based on the concentration of indigestible Ti.

Feed intake and total excreta output are measured quantitatively per cage over four consecutive days (from day 17 to 20) for the determination of nitrogen-corrected apparent metabolizable energy (AMEn) and Nitrogen retention. Daily excreta collections are pooled within a cage, mixed in a blender and sub-sampled. Each sub sample is lyophilized, ground to pass through a 0.5 mm sieve and stored in airtight plastic containers at −4 C pending analysis. Processed samples are analysed for DM, GE, N, and soluble and insoluble NSPs as per standard procedures.

Means are separated using pair wise t-tests. Significant differences are considered at $P<0.05$. Cages are used as the experimental unit.

Results

Preliminary results indicate that the combination of protease+phytase and every one of the tested DFMs exhibit a greater ileal digestibility of energy, N, starch, fat, and/or soluble and insoluble NSPs compared to the negative control treatment and protease+phytase and/or each of the DFMs by themselves. The combination of protease+phytase and every one of the tested DFMs exhibit a greater AME, nitrogen retention, and total tract disappearance of soluble and insoluble NSPs compared to the negative control treatment and protease+phytase and/or each of the DFMs by themselves.

Example 4

Materials and Methods

Tissue samples were taken from broiler chicks from the trial presented in Example 1 at 23 days of age. Treatment specifications are presented in Table 1. The jejunum, pancreas and liver were removed from 2 birds from every pen and the mucosa pooled resulting in eight samples per treatment. The samples were rinsed in buffer solution (PBS) immersed in a tissue storage reagent (RNAlater) according to manufacturer's protocol and stored at −80° C. Total RNA was isolated from each tissue sample using a single step phenol-chloroform extraction method as described by Chomczynski and Saachi (1987; Anal. Biochem. 162:156-9). Concentration of the RNA was determined by measuring the absorbance at 260 nm (Nanodrop) and monitored for integrity by gel electrophoresis on 1.2% agarose gels. Only RNA of sufficient purity and having a ratio of absorption at 260 nm vs. 280 nm greater than 1.87 were considered for use.

Microarrays were manufactured using 70 base pair oligonucleotides (Opereon Biotechnologies Inc) according to the protocol described by Druyan et al. (2008; Poult. Sci. 87:2418-29). The experimental design of the array was a complete interwoven loop design as described by Garosi et al. (2005; Br. J. Nutr. 93:425-32) which each sample is compared directly with the others in a multiple pair wise fashion allowing all treatments to be compared. The samples were labelled according to the method described by Druyan et al. (2008; Poult. Sci. 87:2418-29) in that that half the samples would be labelled with Cy3 and half with Cy5 which are fluorescent dyes of cyanine. Hybridisation was carried out using the Pronto Plus! Microarray Hybridisation Kit prior to the addition of Cy3 and Cy5 labelled cDNA probes and covered with a clean glass coverslip (Lifterslip) and left to hybridise for 16 hours. The microarrays were then scanned on a Scan Array Gx PLUS Microarray Scanner set to 65% laser power to acquire images.

Total RNA from individual samples was reversed transcribed to produce cDNA which was then used as a template for the qPCR amplifications as described by Druyan et al. (2008; Poult. Sci. 87:2418-29). Thermocycling parameters were optimised for each gene and each gene was amplified independently in duplicate within a single instrument run.

Data files were generated from the scanned images of the microarrays but extracting the intensity raw data for each slide and dye combination using ScanAlyze Softare. Intensity data files were then analysed using JMP Genomics including and initial log2 transformation. Data normalisation was performed using locally-weighted regression and smoothing first within array and across all arrays. The resulting normalised log2 intensities were analysed using a mixed model ANOVA.

Mean intensities were compared using a threshold of significance based on Bongerroni correction of P=0.05 (Hochberg 1998). For the complete array, including all replicates, a mean by grid intensity was calculated for each gene using the 3 side by side probes, resulting in a total of four replicated means, one from each grid, per gene. Data for the Ct ratio from the samples in duplicate (sample gene Ct: Sample GAPDH Ct) depending on treatment were subjected to one way ANOVA.

Results

Expression data was collected using the microarray platform and a "heat map" produced to visualise the data for jejunum (FIG. 7) and pancreas (FIG. 8) at 23 days of age. Relative expression levels of six genes of interest were converted to visual cues based on the scale seen in FIG. 7. Lowly expressed genes are marked with a minus sign ("−"), and highly expressed genes are marked with a plus sign ("+"); whereas a greater gray intensity depicts a greater difference from the mean expression level of the treatments. The genes that were measured and their purported functions are seen in Table 7. Real-time PCR was used to validate the gene expression shown in the heat map for sucrase iso-maltase (SI) and fatty acid synthase (FASN) and were highly correlated to the array data.

TABLE 7

Purported function of genes measured.

| Gene | Identity | Function |
| --- | --- | --- |
| ACACA | Acetyl-CoA carboxylase A | Fatty acid biosynthesis |
| GCK | Glucokinase | Initial step in glucose metabolism |
| SI | Sucrase isomaltase | Glucose metabolism |
| PEPT1 | Oligo-peptide transporter 1 | Oligo-peptide transport |
| ZO1 | Tight Junction protein 1 | Tight junction formation, intestinal integrity |
| CD3d | T- cell antigen CD3 | T-cell marker |
| FASN | Fatty acid synthase | Fatty acid biosynthesis |

Figure 7:
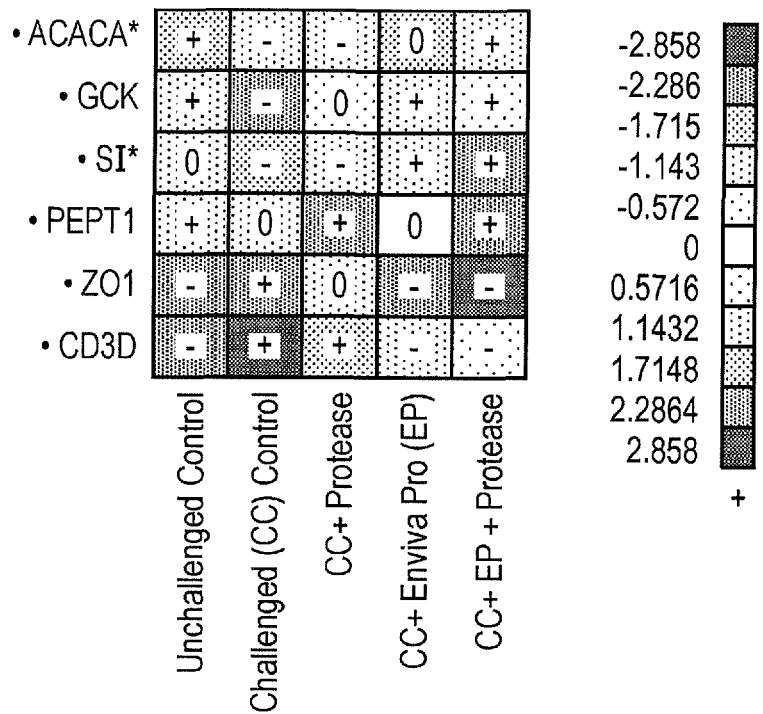
FIG. 7 shows a heat map of expression profiles of genes of interest for all treatments for jejunum at 23 days of age.
Unchallenged control=Unchallenged Control+phytase
CC=Challenged Control+phytase
CC+Protease=Challenged Control+phytase+protease
CC+EP=Challenged Control+phytase+Enviva Pro
CC+EP+Protease=Challenged Control+phytase+protease+Enviva Pro.

FIG. 7 shows a heat map of expression profiles of genes of interest for all treatments for jejunum at 23 days of age.

Figure 8:
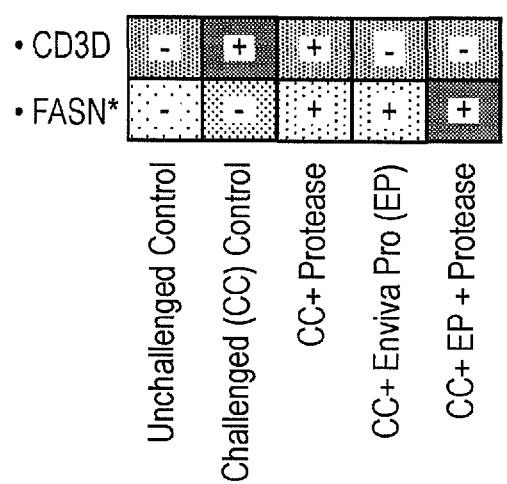
FIG. 8 shows a heat map of expression profile of chicken alpha amylase for all treatments in pancreas at 23 days of age.
Unchallenged control=Unchallenged Control+phytase
CC=Challenged Control+phytase
CC+Protease=Challenged Control+phytase+protease
CC+EP=Challenged Control+phytase+Enviva Pro
CC+EP+Protease=Challenged Control+phytase+protease+Enviva Pro.

FIG. 8 shows a heat map of expression profile of genes of interest for all treatments in liver at 23 days of age.

In FIGS. 7 and 8 the key is as follows:
Unchallenged control=Unchallenged Control+phytase
CC=Challenged Control+phytase
CC+Protease=Challenged Control+phytase+protease
CC+EP=Challenged Control+phytase+Enviva Pro
CC+EP+Protease=Challenged Control+phytase+protease+Enviva Pro The expression of acetyl CoA carboxylase A (ACACA) was down-regulated in the challenged control but the combination of protease+phytase and Enviva Pro increased this to a level comparable with the unchallenged control treatment. Enviva Pro with only phytase or a protease+phytase without Enviva Pro did not have as noticeable an effect as the combination. ACACA is involved in the production of fatty acids from acetyl CoA and is used as a marker of lipogenesis.

The expression of Glucokinase (GCK) was down-regulated in the challenged control but the combination of protease+phytase with Enviva Pro produced an up-regulation similar to the unchallenged control. The extent of the up-regulation was greater than when protease+phytase were used without a DFM. A similar pattern was also seen with sucrase iso-maltase (SI) where the combination of Enviva Pro with protease+phytase increased expression compared to both the challenged and unchallenged control. GCK is a key enzyme in glucose metabolism and SI is responsible for hydrolysis of sucrose and iso-maltose, and so has an important role in the digestion and absorption of carbohydrates in animals.

The expression of oligo-peptide transport 1 (PEPT1) was increased by protease+phytase alone and when in combination with Enviva Pro. PEPT1 is part of a peptide transport system and is responsible for the uptake of a wide range of di- and tri-peptides.

Tight Junction protein 1 (ZO1) was most highly expressed in the challenged control. A reduction was seen with protease+phytase but a greater down-regulation in expression was seen with protease+phytase in combination with Enviva Pro which caused a greater reduction than that seen in the unchallenged control. ZO1 is a protein that is on the cytoplasmic face of tight junctions, there are various roles for this protein ranging from signal transduction for tight junction assembly to stability of the tight junctions themselves.

The T-cell antigen CD3 (CD3D) was highly expressed in the challenged control. The protease+phytase treatment had some effect in reducing the expression of this gene, but a greater effect was seen when protease+phytase were used in combination with Enviva Pro. The same results were seen in the jejunum and the liver for CD3D which strengthen the results. CD3D is a surface molecule found on T cells and plays an important role in signal transduction during T-cell receptor engagement and is part of the T-cell receptor/CD3 complex.

Fatty acid synthase (FASN) was down-regulated in the challenged control, whereas protease+phytase, and Enviva Pro up-regulated this gene. The combination of Enviva Pro and protease+phytase increased it even more. FASN is a key enzyme for fatty acid synthesis and is involved in catalysing the production of long chain saturated fatty acids.

Discussion

The increase of acetyl CoA carboxylase expression due to the addition of Enviva Pro and protease+phytase in comparison to the challenged control suggests that there was increased lipogenesis. This would occur if carbohydrate availability and digestion is higher which means there is increased energy surplus which is diverted to fat transport and storage. The increase in expression of glucokinase and sucrase isomerase with the combination of protease+phytase and Enviva Pro suggests that there was increased absorption of glucose, and increased availability of sucrose and isomaltose in the brush border, which indicates a positive interaction between the enzyme and DFMs to increase carbohydrate absorption in the small intestine and thus increase energy availability from the diet. Additionally, the decreased glucokinase expression for the challenged control suggests that the *Clostridium perfringens* challenge caused damage to the mucosa and that addition of Enviva Pro and protease+phytase may have acted to remedy this. The increase in expression of the peptide transporter oligopeptide transporter 1 (PEPT1) when protease+phytase alone and in combination with Enviva Pro suggests increased availability of peptides and thus an increased requirement for transport, which indicates an effect of enzymes and DFMs to increase the availability of peptides for the animal which allows for greater growth.

The increased fatty acid synthase (FASN) expression in the liver and the increased acetyl CoA carboxylase A in the jejunum suggest increased fatty acid synthesis due to increased carbohydrate availability. Enzymes and Enviva Pro acted together to produce more available energy for the animal which resulted in more growth.

The effect of Enviva Pro on reducing the expression of Tight junction protein 1 indicates lower requirement for protein turn over, which may be related to a high intestinal integrity. The increased expression in the challenged control, however, suggests that turnover/requirement of the protein was high due to failing intestinal integrity possibly due to the coccidia and *Clostridium perfringens* infection. The effect of a combination of protease+phytase (without Enviva Pro) or the effect of Enviva Pro with phytase alone on down-regulating ZO1 is not as evident as the combination of protease+phytase+Enviva Pro. This indicates that Enviva Pro and protease+phytase in combination acts to increase intestinal integrity and thus benefit the intestinal health of the animal. Increased intestinal integrity, and thus absorptive capacity, appears to be one of the mechanisms by which the effectiveness of exogenous enzymes is increased when a DFM is present.

The increased expression of T cell antigen CD3 d in the challenged control indicates increased cell-mediated immune response due to the challenge. In these conditions, birds will be undergoing sub-optimal performance because the immune response will demand energy that could be used for growth, and because some birds will experience a systemic disease response. The increased expression of this immunological marker is markedly reversed when Enviva Pro is used with phytase alone or in combination with protease+phytase. Down regulation of immune response in the intestine may be one of the mechanisms by which the effectiveness of exogenous enzymes in nutrient absorption and performance is increased when a DFM is present, particularly in situations of enteric disease challenge.

The net effect of a down-regulated immune response and higher intestinal integrity, and a better nutrient digestion and absorption with the combination of enzymes and DFMs, clearly determines enhanced production performance of broiler chickens.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for reducing necrotic enteritis lesion scores in a subject comprising administering to the subject a feed additive composition comprising a direct fed microbial (DFM) in combination with a protease and a phytase,
    wherein the DFM is present at a dosage of between $3.75 \times 10^7$ CFU/g feed additive composition and $1 \times 10^{11}$ CFU/g feed additive composition, the protease is present at a dosage of between 1000PU/g feed additive composition and 60,000PU/g feed additive composition, and the phytase is present at a dosage of between 200FTU/g feed additive composition and 40,000 FTU/g feed additive composition,
    wherein the DFM comprises *Bacillus* strains 15A-P4 (PTA-6507); 2084 (NRRL B-500130); and LSSA01 (NRRL-B-50104), and
    wherein the subject is poultry.

2. The method according to claim 1 wherein the direct fed microbial is an antipathogen direct fed microbial.

3. The method according to claim 1 wherein the direct fed microbial is in the form of an endospore.

4. The method according to claim 1 wherein the protease is a subtilisin, a bacillolysin, an alkaline serine protease, a keratinase, or a Nocardiopsis protease.

5. The method according to claim 1 wherein the phytase is a 6-phytase or a 3-phytase.

6. The method according to claim 5 wherein the phytase is a 6-phytase.

7. The method according to claim 1 wherein the phytase is an *E. coli* phytase or a *Buttiauxella* phytase or *Hafnia* phytase or *Citrobacter* phytase or an *Aspergillus* phytase or a *Penicillium* phytase or a *Trichoderma* phytase or an *E. coli* phytase or a *Hansenula* phytase.

* * * * *